(12) United States Patent
Onik et al.

(10) Patent No.: US 11,141,216 B2
(45) Date of Patent: Oct. 12, 2021

(54) RADIO-FREQUENCY ELECTRICAL MEMBRANE BREAKDOWN FOR THE TREATMENT OF HIGH RISK AND RECURRENT PROSTATE CANCER, UNRESECTABLE PANCREATIC CANCER, TUMORS OF THE BREAST, MELANOMA OR OTHER SKIN MALIGNANCIES, SARCOMA, SOFT TISSUE TUMORS, DUCTAL CARCINOMA, NEOPLASIA, AND INTRA AND EXTRA LUMINAL ABNORMAL TISSUE

(71) Applicant: ImmunSYS, Inc., Fort Lauderdale, FL (US)

(72) Inventors: Gary M Onik, Ft. Lauderdale, FL (US); James A. Miessau, Branford, CT (US); David G. Bostwick, Orlando, FL (US)

(73) Assignee: ImmunSys, Inc., Fort Lauderdale, FL (US)

( * ) Notice: Subject to any disclaimer, the term of this patent is extended or adjusted under 35 U.S.C. 154(b) by 0 days.

(21) Appl. No.: 15/547,631

(22) PCT Filed: Feb. 1, 2016

(86) PCT No.: PCT/US2016/015944
§ 371 (c)(1),
(2) Date: Jul. 31, 2017

(87) PCT Pub. No.: WO2016/123608
PCT Pub. Date: Aug. 4, 2016

(65) Prior Publication Data
US 2018/0263685 A1   Sep. 20, 2018

Related U.S. Application Data

(60) Provisional application No. 62/111,870, filed on Feb. 4, 2015, provisional application No. 62/110,702, filed (Continued)

(51) Int. Cl.
*A61B 18/14* (2006.01)
*A61B 18/18* (2006.01)
(Continued)

(52) U.S. Cl.
CPC ...... *A61B 18/1477* (2013.01); *A61B 10/0233* (2013.01); *A61B 18/18* (2013.01); (Continued)

(58) Field of Classification Search
CPC . A61B 18/1477; A61B 18/18; A61B 10/0233; A61B 2034/2051; (Continued)

(56) References Cited

U.S. PATENT DOCUMENTS 4,483,338 A   11/1984   Bloom
5,139,496 A   8/1992   Hed et al.
(Continued)

FOREIGN PATENT DOCUMENTS

CN   103118678   5/2013
JP   2001523987   11/2001
(Continued)

OTHER PUBLICATIONS

JP Office action in Japanese Appln. No. 2016-536858, dated Nov. 12, 2019, 29 pages (with english translation).
(Continued)

*Primary Examiner* — Linda C Dvorak
*Assistant Examiner* — Annabeth E Rodriguez
(74) *Attorney, Agent, or Firm* — Fish & Richardson P.C.

(57) ABSTRACT

An imaging, guidance, planning and treatment system integrated into a single unit or assembly of components, and a
(Continued)

method for using same, that can be safely and effectively deployed to treat prostate cancer in all medical settings, including in a physician's office or in an outpatient setting. The system utilizes the novel process of Radio-Frequency Electrical Membrane Breakdown ("EMB" or "RFEMB") to destroy the cellular membranes of unwanted or cancerous tissue without denaturing the intra-cellular contents of the cells comprising the tissue, thereby exposing tumor antigens and other intra-cellular components which can have an immunologic effect on local or distant cancerous tissue, with or without the addition of immunologic adjuvant drugs. The system preferably comprises at least one EMB treatment probe 20, at least one trackable biopsy needle 200, at least one trackable anesthesia needle 300, and at least one controller unit for at least partially automating the treatment process.

21 Claims, 28 Drawing Sheets

Related U.S. Application Data on Feb. 2, 2015, provisional application No. 62/110,733, filed on Feb. 2, 2015, provisional application No. 62/110,646, filed on Feb. 2, 2015, provisional application No. 62/110,674, filed on Feb. 2, 2015, provisional application No. 62/109,965, filed on Jan. 30, 2015.

(51) Int. Cl.
 *A61B 18/00* (2006.01)
 *A61B 34/20* (2016.01)
 *A61B 10/02* (2006.01)

(52) U.S. Cl.
 CPC ........... *A61B 2018/00196* (2013.01); *A61B 2018/00577* (2013.01); *A61B 2018/00994* (2013.01); *A61B 2018/1475* (2013.01); *A61B 2034/2051* (2016.02)

(58) Field of Classification Search
 CPC .. A61B 2018/1475; A61B 2018/00577; A61B 2018/00196; A61B 2018/00994; A61B 2018/0418; A61B 2018/0761; A61B 2018/0577; A61B 2018/00821; A61B 2018/0988; A61B 18/12; A61B 18/00
 See application file for complete search history.

(56) References Cited

U.S. PATENT DOCUMENTS

| | | | |
|---|---|---|---|
| 5,575,811 A | 11/1996 | Reid | |
| 5,672,174 A * | 9/1997 | Gough | A61B 18/1477 606/41 |
| 5,931,807 A | 8/1999 | McClure | |
| 6,214,297 B1 | 4/2001 | Zhang et al. | |
| 6,241,702 B1 | 6/2001 | Lundquist | |
| 6,379,348 B1 | 4/2002 | Onik | |
| 6,408,199 B1 * | 6/2002 | Goldin | A61B 18/1492 600/374 |
| 6,482,619 B1 | 11/2002 | Rubinsky et al. | |
| 6,505,629 B1 | 1/2003 | Mikus et al. | |
| 6,575,969 B1 | 6/2003 | Rittman, III et al. | |
| 6,623,480 B1 | 9/2003 | Kuo et al. | |
| 6,978,174 B2 | 12/2005 | Gelfand et al. | |
| 7,113,821 B1 * | 9/2006 | Sun | A61B 5/14514 424/489 |
| 7,162,303 B2 | 1/2007 | Levin et al. | |
| 7,572,623 B2 | 8/2009 | Mangano et al. | |
| 7,620,451 B2 * | 11/2009 | Demarais | A61N 1/05 607/3 |
| 7,653,438 B2 | 1/2010 | Deem et al. | |
| 7,680,543 B2 * | 3/2010 | Azure | A61B 18/1477 606/41 |
| 7,744,878 B2 | 6/2010 | Mather | |
| 7,853,333 B2 | 12/2010 | Demarais | |
| 7,937,143 B2 | 5/2011 | Demarais et al. | |
| 7,938,824 B2 | 5/2011 | Chomenky | |
| 8,048,067 B2 | 11/2011 | Davalos et al. | |
| 8,114,070 B2 | 2/2012 | Rubinsky et al. | |
| 8,131,371 B2 | 3/2012 | Demarais et al. | |
| 8,145,316 B2 | 3/2012 | Deem et al. | |
| 8,221,411 B2 | 7/2012 | Francischelli et al. | |
| 8,226,648 B2 | 7/2012 | Paul et al. | |
| 8,231,603 B2 | 7/2012 | Hobbs et al. | |
| 8,282,631 B2 | 10/2012 | Davalos et al. | |
| 8,465,484 B2 | 6/2013 | Davalos et al. | |
| 8,814,860 B2 * | 8/2014 | Davalos | A61N 1/327 606/41 |
| 9,545,523 B2 | 1/2017 | Nanda | |
| 9,598,491 B2 | 3/2017 | Ahmed et al. | |
| 10,154,869 B2 | 12/2018 | Onik et al. | |
| 10,448,989 B2 | 10/2019 | Arena et al. | |
| 10,849,678 B2 | 12/2020 | Onik et al. | |
| 2001/0044596 A1 | 11/2001 | Jaafar | |
| 2002/0019644 A1 | 2/2002 | Hastings et al. | |
| 2002/0086014 A1 | 7/2002 | Korman et al. | |
| 2002/0087151 A1 | 7/2002 | Mody et al. | |
| 2002/0095124 A1 | 7/2002 | Palasis et al. | |
| 2002/0111617 A1 | 8/2002 | Cosman et al. | |
| 2002/0128640 A1 | 9/2002 | Swanson et al. | |
| 2002/0183684 A1 | 12/2002 | Dev et al. | |
| 2002/0193784 A1 | 12/2002 | McHale et al. | |
| 2002/0193789 A1 | 12/2002 | Underwood et al. | |
| 2003/0018329 A1 | 1/2003 | Hooven | |
| 2003/0045495 A1 | 3/2003 | Li et al. | |
| 2003/0055471 A1 | 3/2003 | Fenn et al. | |
| 2003/0093067 A1 | 5/2003 | Panescu | |
| 2003/0153960 A1 | 8/2003 | Chornenky | |
| 2003/0163040 A1 | 8/2003 | Gidlenberg | |
| 2003/0216722 A1 | 11/2003 | Swanson et al. | |
| 2003/0216792 A1 | 11/2003 | Levin et al. | |
| 2004/0143261 A1 | 7/2004 | Hartley et al. | |
| 2004/0248842 A1 | 12/2004 | Wagner et al. | |
| 2005/0182462 A1 | 8/2005 | Chomenky et al. | |
| 2005/0214268 A1 | 9/2005 | Cavanagh et al. | |
| 2005/0221270 A1 | 10/2005 | Connelly et al. | |
| 2005/0261672 A1 | 11/2005 | Deem | |
| 2005/0288667 A1 | 12/2005 | Thompson et al. | |
| 2005/0288730 A1 * | 12/2005 | Deem | A61B 8/12 607/42 |
| 2006/0041277 A1 | 2/2006 | Deem et al. | |
| 2006/0073589 A1 | 4/2006 | Belardelli et al. | |
| 2006/0149147 A1 | 7/2006 | Yanof | |
| 2006/0161246 A1 | 7/2006 | Rhim et al. | |
| 2006/0293725 A1 | 12/2006 | Rubinsky et al. | |
| 2006/0293730 A1 | 12/2006 | Rubinsky et al. | |
| 2007/0043345 A1 | 2/2007 | Davalos et al. | |
| 2007/0049919 A1 | 3/2007 | Lee | |
| 2007/0060989 A1 | 3/2007 | Deem | |
| 2007/0066957 A1 | 3/2007 | Demarais et al. | |
| 2007/0083193 A1 * | 4/2007 | Werneth | A61B 5/7445 606/41 |
| 2007/0083239 A1 | 4/2007 | Demarais et al. | |
| 2007/0129720 A1 | 6/2007 | Demarais et al. | |
| 2007/0129760 A1 | 6/2007 | Demarais | |
| 2007/0233057 A1 | 10/2007 | Konishi | |
| 2008/0033417 A1 | 2/2008 | Nields et al. | |
| 2008/0058706 A1 | 3/2008 | Zhang et al. | |
| 2008/0071265 A1 | 3/2008 | Azure | |
| 2008/0132884 A1 * | 6/2008 | Rubinsky | A61B 18/1477 606/34 |
| 2008/0132885 A1 | 6/2008 | Rubinsky et al. | |
| 2008/0208052 A1 | 8/2008 | LePivert et al. | |
| 2008/0247506 A1 | 10/2008 | Maschke | |
| 2008/0306476 A1 | 12/2008 | Hennings et al. | |
| 2008/0319375 A1 | 12/2008 | Hardy | |

(56) References Cited

U.S. PATENT DOCUMENTS

| | | |
|---|---|---|
| 2009/0088648 A1* | 4/2009 | Jaffe ............... A61B 5/0084 600/466 |
| 2009/0118727 A1 | 5/2009 | Pearson et al. |
| 2009/0143717 A1 | 6/2009 | Bass |
| 2009/0177094 A1 | 7/2009 | Brown et al. |
| 2009/0292342 A1 | 11/2009 | Rubinsky et al. |
| 2009/0326366 A1 | 12/2009 | Krieg |
| 2010/0023004 A1 | 1/2010 | Francischelli et al. |
| 2010/0030211 A1 | 2/2010 | Davalos et al. |
| 2010/0049178 A1 | 2/2010 | Deem |
| 2010/0069833 A1 | 3/2010 | Wenderow et al. |
| 2010/0100092 A1 | 4/2010 | Turner et al. |
| 2010/0049031 A1 | 5/2010 | Fruland et al. |
| 2010/0152725 A1 | 6/2010 | Pearson et al. |
| 2010/0179530 A1 | 7/2010 | Long et al. |
| 2010/0249771 A1 | 9/2010 | Pearson et al. |
| 2010/0250209 A1 | 9/2010 | Pearson et al. |
| 2010/0261944 A1 | 10/2010 | Davalos et al. |
| 2010/0262067 A1 | 10/2010 | Chomenky et al. |
| 2010/0274178 A1 | 10/2010 | LePivert et al. |
| 2010/0331758 A1 | 12/2010 | Davalos et al. |
| 2011/0015630 A1 | 1/2011 | Azure |
| 2011/0082534 A1 | 4/2011 | Wallace |
| 2011/0106221 A1 | 5/2011 | Neal, II et al. |
| 2011/0112520 A1 | 5/2011 | Michael |
| 2011/0160514 A1 | 6/2011 | Long et al. |
| 2011/0160614 A1 | 6/2011 | Long et al. |
| 2011/0166499 A1 | 7/2011 | Demarais et al. |
| 2011/0190659 A1 | 8/2011 | Long et al. |
| 2011/0190764 A1 | 8/2011 | Long et al. |
| 2011/0202053 A1 | 8/2011 | Moss et al. |
| 2012/0021481 A1 | 1/2012 | Hebner et al. |
| 2012/0041525 A1 | 2/2012 | Karni |
| 2012/0071749 A1 | 3/2012 | Xu et al. |
| 2012/0071872 A1 | 3/2012 | Rubinsky et al. |
| 2012/0071874 A1 | 3/2012 | Davalos et al. |
| 2012/0109122 A1* | 5/2012 | Arena ............... A61B 18/14 606/41 |
| 2012/0143181 A1 | 6/2012 | Demarais et al. |
| 2012/0190040 A1 | 7/2012 | Talebpour et al. |
| 2012/0215218 A1 | 8/2012 | Lipani |
| 2012/0215221 A1 | 8/2012 | Woloszko |
| 2012/0220998 A1 | 8/2012 | Long et al. |
| 2012/0220999 A1 | 8/2012 | Long |
| 2012/0221002 A1 | 8/2012 | Long et al. |
| 2012/0230939 A1 | 9/2012 | Perambakam et al. |
| 2012/0252087 A1 | 10/2012 | Hebner et al. |
| 2012/0253188 A1 | 10/2012 | Holland |
| 2012/0277741 A1 | 11/2012 | Davalos et al. |
| 2012/0277763 A1 | 11/2012 | Greenblatt |
| 2013/0108667 A1 | 3/2013 | Wang et al. |
| 2013/0101551 A1 | 4/2013 | Har-Noy |
| 2013/0071905 A1 | 5/2013 | Soikum et al. |
| 2013/0110098 A1 | 5/2013 | Lalonde |
| 2013/0184702 A1 | 7/2013 | Neal, II et al. |
| 2013/0189301 A1 | 7/2013 | Har-Noy |
| 2013/0211230 A1 | 8/2013 | Sperling |
| 2013/0237984 A1 | 9/2013 | Sklar |
| 2013/0289369 A1 | 10/2013 | Margolis |
| 2013/0295110 A1 | 11/2013 | Binder et al. |
| 2013/0302409 A1 | 11/2013 | Fuchs et al. |
| 2013/0304062 A1 | 11/2013 | Chan et al. |
| 2013/0310823 A1 | 11/2013 | Gefland et al. |
| 2013/0345697 A1 | 12/2013 | Garcia et al. |
| 2014/0012251 A1 | 1/2014 | Himmelstein et al. |
| 2014/0039491 A1 | 2/2014 | Basok et al. |
| 2014/0088578 A1 | 3/2014 | Rubinsky et al. |
| 2014/0172054 A1 | 6/2014 | Zarins et al. |
| 2014/0205609 A1 | 7/2014 | Valentine |
| 2014/0234296 A1 | 8/2014 | Sharma et al. |
| 2014/0257272 A1 | 9/2014 | Clark et al. |
| 2014/0328833 A1 | 11/2014 | Korman et al. |
| 2014/0350537 A1 | 11/2014 | Baust et al. |
| 2014/0356397 A1 | 12/2014 | Akle et al. |
| 2015/0150618 A1 | 6/2015 | Onik et al. |
| 2015/0190505 A1 | 7/2015 | Yeung |
| 2015/0201996 A1 | 7/2015 | Rubisky |
| 2015/0265705 A1 | 9/2015 | Li et al. |
| 2015/0374436 A1 | 12/2015 | Subramaniam et al. |
| 2016/0128767 A1 | 5/2016 | Azamian et al. |
| 2016/0346354 A1 | 12/2016 | Heslet et al. |
| 2016/0367310 A1 | 12/2016 | Onik et al. |
| 2017/0020931 A1 | 1/2017 | Zhou et al. |
| 2017/0143780 A1 | 5/2017 | Zitvogel et al. |
| 2018/0021084 A1 | 1/2018 | Onik et al. |
| 2018/0028260 A1 | 2/2018 | Onik et al. |
| 2018/0028267 A1 | 2/2018 | Onik et al. |
| 2018/0133319 A1 | 5/2018 | Vo-Dinh et al. |
| 2018/0154142 A1 | 6/2018 | Guo et al. |
| 2018/0318365 A1 | 11/2018 | Yeung et al. |
| 2018/0318393 A1 | 11/2018 | Pierce et al. |
| 2019/0023804 A1 | 1/2019 | Onik et al. |
| 2019/0183561 A1 | 6/2019 | Hobbs et al. |
| 2019/0209652 A1 | 7/2019 | Pierce et al. |
| 2019/0241658 A1 | 8/2019 | Frederick |
| 2019/0298770 A1 | 10/2019 | Rabinovich et al. |
| 2020/0038093 A1 | 2/2020 | Onik |
| 2020/0040095 A1 | 2/2020 | Onik et al. |
| 2020/0277379 A1 | 9/2020 | Bostwick et al. |
| 2021/0177491 A1 | 6/2021 | Onik et al. |

FOREIGN PATENT DOCUMENTS

| | | |
|---|---|---|
| JP | 2006187446 | 7/2006 |
| JP | 2009-297527 | 12/2009 |
| JP | 2010500153 | 1/2010 |
| JP | 2013/531043 | 8/2013 |
| JP | 2015-38492 A | 2/2015 |
| WO | WO 2004/037313 | 5/2004 |
| WO | WO 2008/034103 | 3/2008 |
| WO | WO 2010/080974 | 7/2010 |
| WO | WO 2012/088149 | 6/2012 |
| WO | WO 2012/99974 | 7/2012 |
| WO | WO 2013/053775 | 4/2013 |
| WO | WO 2013/079980 | 6/2013 |
| WO | WO 2014/149690 | 9/2014 |
| WO | WO 2015/085162 | 6/2015 |
| WO | WO 2015/125159 | 8/2015 |
| WO | WO 2015/140150 | 9/2015 |
| WO | WO 2015/153639 | 10/2015 |
| WO | WO 2016/123608 | 8/2016 |
| WO | WO 2016/126778 | 8/2016 |
| WO | WO 2016/126811 | 8/2016 |
| WO | WO 2016/126905 | 8/2016 |
| WO | WO 2016/127162 | 8/2016 |
| WO | WO 2017/123981 | 7/2017 |

OTHER PUBLICATIONS

Al Sakere et al., "A study of the immunological response to tumor ablation with irreversible electroporation," Technol Cancer Res Treat., Aug. 2007, 6(4):301-306.

Ammar et al., "Impact of a pulsed electric field on damage of plant tissues: effects of cell size and tissue electrical conductivity," J Food Sci., Jan.-Feb. 2011, 76(1):E90-7.

Arena et al. "High-Frequency Irreversible Electroporation (H-FIRE) for Non-Thermal Ablation without Muscle Contraction", Biomed Eng. Online Nov. 21, 2011, 10:102.

Aronsson et al., "Inactivation of *Escherichia coli*, Listeria innocua and *Saccharomyces cerevisiae* in relation to membrane permeabilization and subsequent leakage of intracellular compounds due to pulsed electric field processing," Int J Food Microbiol., Mar. 1, 2005, 99(1):19-32.

Asavasanti et al., "Critical electric field strengths of onion tissues treated by pulsed electric fields," J Food Sci., Sep. 2010, 75(7):E433-43.

Asavasanti et al., "Permeabilization of plant tissues by monopolar pulsed electric fields: effect of frequency," J Food Sci. Jan.-Feb. 2011, 76(1):E98-111.

Au et al., "Irreversible electroporation facilitates gene transfer of a GM-CSF plasmid with a local and systemic response," Surgery, Sep. 2013, 154(3):496-503.

(56) References Cited

OTHER PUBLICATIONS

Beebe et al., "Non-ionizing radiation with nanosecond pulsed electric fields as a cancer treatment: in vitro studies," Conf Proc IEEE Eng Med Biol Soc., Sep. 2-6, 2009, pp. 6509-6512.
Bertacchini et al., "Design of an irreversible electroporation system for clinical use," Technol Cancer Res Treat., Aug. 2007, 6(4):313-20.
Chang et al. "Changes in Membrane Structure Induced by Electroporation as Revealed by Rapid-Freezing Electron Microscopy", Biophys J., Jul. 1, 1990, 58(1):1-12.
Chang et al., "Construction of a Genomic Map of H. pylori by Pulsed-Field Gel Electrophoresis (PFGE)," Methods Mol Med., 1997, 8:165-176.
Chen et al., "Leukemic cell intracellular responses to nanosecond electric fields," Biochem Biophys Res Commun., Apr. 30, 2004, 317(2):421-427.
Chen et al., "Picosecond pulsed electric fields induce apoptosis in HeLa cells via the endoplasmic reticulum stress and caspase-dependent signaling pathways," Int J Oncol., Mar. 2013, 42(3):963-70.
Chen et al., "Membrane electroporation theories: a review," Med Biol Eng Comput., 2006, 44:5-14.
Chen et al., "Nanosecond electric pulses penetrate the nucleus and enhance speckle formation," Biochem Biophys Res Commun., Dec. 14, 2007, 364(2):220-225.
Crowley "Electrical breakdown of bimolecular lipid membranes as an electromechanical instability," Biophys J., Jul. 1973, 13(7):711-724.
Djunzenova et al., "Effect of electric field pulses on the viability and on the membrane-bound immunoglobulins of LPS-activated murine B-lymphocytes: correlation with the cell cycle," Cymetiy, Jan. 1, 1994, 15(1):35-45.
Dortch et al., "Characterization of pulsed magnetic field therapy in a rat model for rheumatoid arthritis," Biomed Sci Instrum., 2006, 42:302-307, Abstract Only.
Dyson et al., "Kinetic and physical studies of cell death induced by chemotherapeutic agents or hyperthermia," Cell Tissue Kinet., May 1986, 19(3):311-324.
Eppich et al., "Pulsed electric fields for selection of hematopoietic cells and depletion of tumor cell contaminants," Nat Biotechnol., Aug. 2000, 18(8):882-887.
Ersus et al., "Disintegration efficiency of pulsed electric field induced effects on onion (*Allium cepa* L.) tissues as a function of pulse protocol and determination of cell integrity by $^1$H-NMR relaxometry," J Food Sci. Sep. 2010 ,75(7):E444-52.
European Search Report in European Application No. 16744266.4, dated Oct. 18, 2018, 10 pages.
Foltz, "Algae Lysis with Pulsed Electric Fields," California State Polytechnic University, San Luis Obispo 2012, [retrieved on May 13, 2019]retrieved from URL <http://digitalcommons.-calpoly.edu/theses/732/>, 76 pages.
García et al., "Biosynthetic requirements for the repair of sublethal membrane damage in *Escherichia coli* cells after pulsed electric fields," J Appl Microbiol., Mar. 2006, 100(3):428-435.
Garilevich et al., "Outlook for the use of focused shock waves and pulsed electric fields in the complex treatment of malignant neoplasms," Conf Proc IEEE Eng Med Biol Soc. 2006, 1:6370-6372.
Gómez-Ochoa et al., "Pulsed electromagnetic fields decrease proinflammatory cytokine secretion (IL-1β and TNF-α) on human fibroblast-like cell culture," Rheumatol Int., Oct. 2011, 31(10):1283-1289.
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, Jun. 1999, 1(2):123-127.
Gordon et al., "Intracellular hyperthermia. A biophysical approach to cancer treatment via intracellular temperature and biophysical alterations," Med Hypotheses., Jan. 1979, 5(1):83-102.
Grys et al., "Decreasing the thresholds for electroporation by sensitizing cells with local cationic anesthetics and substances that decrease the surface negative electric charge," Cell Mol Biol Lett., Mar. 2014, 19(1):65-76.
Hamid et al., "Safety and tumor responses with lambrolizumab (anti-PD-1) in melanoma," N Engl J Med., Jul. 11, 2013, 369(2):134-144.
Harris "Effects of Tumor-like assay conditions, Ionizing radiation, and hyperthermia on immune lysis of tumor cells by cytotoxic T-lymphocytes," Cancer Res., Aug. 1976, 36(8):2733-2739.
Hillen et al., "Treatment of Metastatic Posterior Vertebral Body Osseous Tumors by Using a Targeted Bipolar Radiofrequency Ablation Device: Technical Note," Radiology, Jun. 13, 2014, 273(1):261-267.
Hua et al., "Intense picosecond pulsed electric fields induce apoptosis through a mitochondrial-mediated pathway in HeLa cells," Mol Med Rep., Apr. 2012, 5(4):981-987.
International Search Report and Written Opinion in International Application No. PCT/US2014/068774, dated Mar. 19, 2015, 15 pages.
International Search Report and Written Opinion in International Application No. PCT/US2016/015944, dated Jul. 29, 2016, 13 pages.
International Search Report and Written Opinion in International Application No. PCT/US2016/016300, dated Jul. 8, 2016, 9 pages.
International Search Report and Written Opinion in International Application No. PCT/US2016/016352, dated Jul. 18, 2016, 9 pages.
International Search Report and Written Opinion in International Application No. PCT/US2016/016501, dated Sep. 2, 2016, 10 pages.
International Preliminary Report on Patentability in International Application No. PCT/US2014/068774, dated Jun. 7, 2016, 13 pages.
International Preliminary Report on Patentability in International Application No. PCT/US2016/015944, dated Aug. 1, 2017, 9 pages.
International Preliminary Report on Patentability in International Application No. PCT/US2016/016300, dated Aug. 8, 2017, 6 pages.
International Preliminary Report on Patentability in International Application No. PCT/US2016/016352, dated Aug. 8, 2017, 6 pages.
International Preliminary Report on Patentability in International Application No. PCT/US2016/016501, dated Aug. 8, 2017, 7 pages.
Iu et al., "Reduction in levels of *Escherichia coli* O157:H7 in apple ciderby pulsed electric fields," J Food Prot., Jul. 2001, 64(7):964-969.
Jaeger et al., "Protective effect of milk constituents and sublethal injuries limiting process effectiveness during PEF inactivation of Lb. rhamnosus," Int J Food Microbiol., Aug. 31, 2009, 134(1-2):154-161.
Jia et al., "Crystal structure of human grancalcin, a member of the penta-EF-hand protein family," J Mol Biol., Jul. 28, 2000, 300(5):1271-81.
Jeffers et al., "Dimethylformamide as an enhancer of cavitation-induced cell lysis in vitro," J Acoust Soc Am., Jan. 1995, 97(1):669-676.
Kawano et al., "Cryoimmunologic Antitumor Effects Enhanced by Dendritic Cells in Osteosarcoma", Clin Orthop Relat Res., May 2010, 468(5):1373-1383.
Kennedy et al., "Cationic Peptide Exposure Enhances Pulsed-Electric-Field-Mediated Membrane Disruption," PLoS One, Mar. 26, 2014, 9(3):e92528.
Kennedy et al., "Quantification of electroporative uptake kinetics and electric field heterogeneity effects in cells," Biophys J., Jun. 2008, 94(12):5018-5027.
Kim et al., "Changes of apoptosis in tumor tissues with time after irreversible electroporation," Biochem Biophys Res Commun., Jun. 14, 2013, 435(4):651-656.
Koga et al., "Interstitial Radiofrequency Hyperthermia for Brain Tumors," Neurol Med Chir., May 1993, 33(5):290-294.
Laufer et al., "Tissue Characterization Using Electrical Impedance Spectroscopy Data: A Linear Algebra Approach," Physiol Measu., 2012, 33:997-1013.

(56) References Cited

OTHER PUBLICATIONS

Lee et al., "Electron microscopic demonstration and evaluation of irreversible electroporation-induced nanopores on hepatocyte membranes," J Vasc Interv Radiol., Jan. 2012, 23(1):107-113.
Li et al., "Immunologic Response to Tumor Ablation with Irreversible Electroporation", PLOS One, Nov. 6, 2012, 7(11):e48749.
Li et al., "The effect of lipid molecular packing stress on cationic liposome-induced rabbit erythrocyte fusion," Biochim Biophys Acta., Jan. 14, 1997, 1323(1):105-116.
Lin et al., "Preparation of antioxidant peptide from egg white protein and improvement of its activities assisted by high-intensity pulsed electric field," J Sci Food Agric., May 2012, 92(7):1554-1561.
Ma et al., "Experimental Study on Residual Tumor Angiogenesis after Cryoablation," Asian Pac J Cancer Prev., 2014, 15(6):2491-2494.
Maor et al., "Irreversible electroporation attenuates neointimal formation after angioplasty," IEEE Trans Biomed Eng., Sep. 2008, 55(9):2268-2274.
Marx et al., "A comparative study on the structure of *Saccharomyces cerevisiae* under nonthermal technologies: high hydrostatic pressure, pulsed electric fields and thermo-sonication," Int J Food Microbiol., Dec. 15, 2011, 151(3)327-337.
Mi et al., "[Effect of steep pulsed electric fields on the immune response of tumor-bearing Wistar mice]," Sheng Wu Yi Xue Gong Cheng Xue Za Zhi., Apr. 2007, 24(2):253-256, Abstract Only.
Miller et al., "Integrated Carbon Fiber Electrodes within Hollow Polymer Microneedles for Transdermal Electrochemical Sensing," Biomicrofluidics., Mar. 30, 2011, 5(1):13415.
Miller et al., "Multiplexed microneedle-based biosensor array for characterization of metabolic acidosis," Talanta., Jan. 15, 2012, 88:739-742.
Milligan et al., "Interstitial Hyperthermia," Med Instrum., May-Jun. 1984, 18(3):175-180, Abstract Only.
Mishra et al., "Electric Property Sensing Biopsy Needle for Prostate Cancer Detection," Prostate, Nov. 2013, 73(15):1603-1613.
Morshed et al., "Electrical lysis: dynamics revisited and advances in On-chip operation,"Crit Rev Biomed Eng., 2013, 41(1):37-50.
Neal et al., "Improved local and systemic anti-tumor efficacy for irreversible electroporation in immunocompetent versus immunodeficient mice," PLOS One., May 24, 2013, 8(5):e64559.
Neal et al. "In Vitro and Numerical Support for Combinatorial Irreversible Electroporation and Electrochemotherapy Glioma Treatment", Annals of Biomedical Engineering, Mar. 2014, 42(3):475-487.
Neumann et al., "Permeability changes induced by electric impulses in vesicular membranes," J Membr Biol., Dec. 29, 1972, 10(3):279-290.
O'Dowd et al., "An assessment of the effect of pulsed electrical fields on tenderness and selected quality attributes of post rigour beef muscle," Meat Sci., Feb. 2013, 93(2):303-309.
Onik et al., "Three-Dimensional Sonographically Monitoring Cryosurgery in a Prostate Phantom," Journal of Ultrasound, 1996, 16:267-270.
Onik et al. "Irreversible Electroporation: Implications for Prostate Ablation", Technology in Cancer Res. and Treatment, Aug. 2007, 6(4): 295-300.
Onik et al. "Long-Term Results of Optimized Focal Therapy for Prostate Cancer: Average 10-Year Follow-Up in 70 Patients," Journal of Men's Health, Jun. 2014, 11(2):64-74.
Oshima et al., "Bacterial sterilization and intracellular protein release by a pulsed electric field," Adv Biochem Eng Biotechnol., Adv Biochem Eng Biotechnol., 2004, 90:113-33.
Persson et al., "A model for evaluating therapeutic response of combined cancer treatment modalities: applied to treatment of subcutaneously implanted brain tumors (N32 and N29) in Fischer rats with pulsed electric fields (PEF) and 60Co-gamma radiation (RT)," Technol Cancer Res Treat., Oct. 1, 2003, 2(5):459-470.
Peper et al., "An impedance-based cytotoxicity assay for real-time and label-free assessment of T-cell-mediated killing of adherent cells," J Immunol Methods, Mar. 2014, 405:192-198.
Poudineh et al., "Three-dimensional, sharp-tipped electrodes concentrate applied fields to enable direct electrical release of intact biomarkers from cells," Lab Chip., May 21, 2014, 14(10):1785-1790.
Ribas et al., "Dendritic cell vaccination combined with CTLA4 blockade in patients with metastatic melanoma," Clin Cancer Res., Oct. 1, 2019, 15(19):6267-6275.
Sabel et al., "Cryo-Immunology: A review of the literature and proposed mechanisms for stumulatory versus suppressive immune responses," Cryobiology, 2009, 58:1-11.
Sabel et al. "Immunologic Response To Cryoablation Of Breast Cancer," Breast Cancer Research and Treatment, Mar. 2005, 90(1):97-104.
Sale et al., "Effects of high electric fields on micro-organisms. 3. Lysis of erythrocytes and protoplasts," Biochim Biophys Acta., Aug. 1968, 163(1):37-43.
Schaft et al., "A new way to generate cytolytic tumor-specific T cells: electroporation of RNA coding for a T cell receptor into T lymphocytes," Cancer Immunol Immunother., Sep. 2006,55(9):1132-1141.
Shen et al., "Abstract 4746: Modulation of suppressive myeloid populations by tasquinimod," Cancer Research, Apr. 15, 2013, 73:4746.
Shipman, "Microneedle Sensors May Allow Real-Time Monitoring of Body Chemistry," Dec. 13, 2011, [retrieved on May 15, 2019] retrieved from URL <https://news.ncsu.edu/2011/12/wmsnarayanmnsensors/>, 3 pages.
Somolinos et al., "Inactivation of *Escherichia coli* by citral," J Appl Microbiol., Jun. 2010,108(6):1928-1939.
Somolinos et al., "sigB absence decreased Listeria monocytogenes EGD-e heat resistance but not its Pulsed Electric Fields resistance," Int J Food Microbiol., Jun. 30, 2010, 141(1-2):32-38.
Stevenson et al., "Relationship between cell membrane potential and natural killer cell cytolysis in human hepatocellular carcinoma cells," Cancer Res., Sep. 1, 1989, 49(17):4842-4845.
Tang et al., "Steep pulsed electric fields modulate cell apoptosis through the change of intracellular calcium concentration," Colloids Surf B Biointerfaces., Jun. 15, 2007, 57(2):209-214.
Traitcheva et al., "Electroporation and alternating current cause membrane permeation of photodynamic cytotoxins yielding necrosis and apoptosis of cancer cells," Bioelectrochemistry., Oct. 2010, 79(2):257-260.
Tarek, "Membrane Electroporation: a molecular dynamics Simulation," Biophys J., 2005, 88:4045-4053.
U.S. Food and Drug Administration, "Kinetics of Microbial Inactivation for Alternative Food Processing Technologies—Pulsed Electric Fields", A Report of the Institute of Food Technologists for the Food and Drug Administration of the U.S. Department of Health and Human Services, Mar. 29, 2000, 108 pages.
Veiga et al., "Exposure of human leukemic cells to direct electric current: generation of toxic compounds inducing cell death by different mechanisms," Cell Biochem Biophys., 2005, 42(1):61-74.
Vora et al., "Interstitial implant with interstitial hyperthermia," Cancer, Dec. 1, 1982, 50(11):2518-2523.
Waitz et al. "Potent Induction of Tumor Immunity by Combining Tumor Cryoablation with Anti-CTLA-4 Therapy", Cancer Res., Jan. 2012, 72(2):430-439.
Wikipedia.com [online], "Irreversible Electroporation," Sep. 8, 2018, retrieved on Sep. 11, 2019, retrieved from URL <https://en.wikipedia.org/wiki/Irreversible_electroporation>, 13 pages.
Williams et al., "Gene therapy approaches to prolonging corneal allograft survival," Expert Opin Biol Ther., Jul. 2004, 4(7):1059-1071.
Wouters et al., "Membrane permeabilization in relation to inactivation kinetics of *Lactobacillus* species due to pulsed electric fields," Appl Environ Microbiol., Jul. 2001, 67(7):3092-3101.
Yuan et al., "Immunologic responses to xenogeneic tyrosinase DNA vaccine administered by electroporation in patients with malignant melanoma," J Immunother Cancer, Nov. 18, 2013, 1:20.

(56) References Cited

OTHER PUBLICATIONS

Zheng et al., "Membrane microfilter device for selective capture, electrolysis and genomic analysis of human circulating tumor cells," J Chromatogr A., Aug. 31, 2007, 1162(2):154-61.
JP Office action in Japanese Appln. No. 2017-540247, dated Nov. 26, 2019, 27 pages (with english translation).
Barnett et al., "Surgical ablation as treatment for the elimination of atrial fibrillation: a meta-analysis," The Journal of thoracic and cardiovascular surgery, May 1, 2006, 131(5):1029-35.
Cox et al,. "The surgical treatment of atrial fibrillation," The Journal of thoracic and cardiovascular surgery. 1991, 101(1-4):402-426, 569-592.
Cummings et al., "Alternative energy sources for the ablation of arrhythmias," Pacing and clinical electrophysiology, May 2005, 28(5):434-43.
Doll et al., "Esophageal perforation during left atrial radiofrequency ablation: is the risk too high?," The Journal of Thoracic and Cardiovascular Surgery, Apr. 1, 2003, 125(4):836-42.
Ninet et al., "Surgical ablation of atrial fibrillation with off-pump, epicardial, high-intensity focused ultrasound: results of a multicenter trial," The Journal of thoracic and cardiovascular surgery, Sep. 1, 2005, 130(3):803-e1.
PCT International Preliminary Report on Patentability in international Appln. No. PCT/US2016/016955, dated Jul. 1, 2016, 6 pages.
PCT International Search Reoprt and Written Opinion in international Appln. No. PCT/US2016/016955, dated Jul. 1, 2016, 9 pages.
Viola et al., "The technology in use for the surgical ablation of atrial fibrillation," InSeminars in Thoracic and Cardiovascular Surgery, Jul. 1, 2002, 14(3):198-205.
U.S. Appl. No. 17/101,434, Onik et al., filed Nov. 23, 2020.
Aarts et al., "Cryoablation and immunotherapy: an overview of evidence on its synergy'," Insights Into Imaging, Dec. 2019, 10(1), 12 pages.
Abdo et al., "Immunotherapy plus cryotherapy: potential augmented abscopal effect for advanced cancers," Frontiers in Oncology, Mar. 28, 2018, 8:85.
AMGen.com, "FDA Approves IMLYGIC™ (Talimogene Laherparepvec) As First Oncolytic Viral Therapy In The US," retrieved Aug. 13, 2020 from URL <https://www.amgen.com/media/news-releases/2015/10/fda-approves-imlygic-talimogene-laherparepvec-as-first-oncolytic-viral-therapy-in-the-us/>, Oct. 27, 2015, 7 pages.
Arora et al., "Neoadjuvant Intratumoral Cytokine-Loaded Microspheres are Superior to Postoperative Autologous Cellular Vaccines in Generating Systematic Anti-Tumor Immunity," Journal of Surgical Oncology 94(5):403-412, dated Oct. 1, 2006.
Bastianpillai et al., "Harnessing the immunomodulatory effect of thermal and non-thermal ablative therapies for cancer treatment," Tumor Biology, Dec. 1, 2015, 36(12):9137-46.
Brooks et al., "Intratumoral injection of GM-CSF in perspective-A review," Journal of Medicine. Jan. 1, 2003, 34(1-6):149-53.
Bulvik et al., "Irreversible electroporation versus radiofrequencv ablation: a comparison of local and systemic effects in a small-animal model." Radiology, Aug. 2016, 280(2):413-24.
Chang et al., "Blocking of the PD-1/PD-L1 Interaction by ad-Peptide Antagonist for Cancer Immunotherapv," Angewandte Chemie International Edition, Sep. 28. 2015, 54(40):11760-4.
EP European Search Report in European U.S. Appl. No. 17/739,066, dated Aug. 13, 2019, 23 pages.
EP Extended Search Report in European Appln. No. 17739066.3, dated Dec. 16, 2019, 20 pages.
Fehres et al,. "Understanding the biologv of antigen cross-presentation for the design of vaccines against cancer," Frontiers in immunology. Apr. 8, 2014, 5:149.
Hebb etal, "Systemic Antitumor Effects of Intratumoral Administration of the Novel Immunotherapeutic Combination Anti-CTLA4, Anti-CD137, and Anti-0X40 in Mouse Models of Lymphoma and Solid Tumor," Blood Journal, Dec. 3, 2015 126(23):1552.
Immuno-OncologyNews.com, "Cryoablation Combined With Intratumoral Injection of Immunotherapeutic Drags Offers Promising Outcomes," Feb. 10, 2015, 2 pages.
Ito et al., "Immune adjuvant activity of pre-resectional radiofrequency ablation protects against local and systemic recurrence in aggressive murine colorectal cancer," PLoS One, Nov. 23, 2015, 10(11):e0143370, 23 pages.
Jonathan et al., "Systemic Antitumor Effects of Intratumoral Administration of the Novel Immunotherapeutic Combination Anti-CTLA4, Anti-CD137, and Anti-OX40 in Mouse Models of Lymphoma and Solid Tumor," Blood, Jan. 1, 2015, 126(23):1552.
Koster et al., "Recent developments and future challenges in immune checkpoint inhibitory cancer treatment," Current opinion in oncology, Nov. 1, 2015, 27(6):482-8.
Machlenkin et al., "Combined dendritic cell cryotherapy of tumor induces systemic antimetastatic immunity," Clinical Cancer Research, Jul. 1, 2005, 11(13):4955-61.
Marabelle et al., "Intratumoral anti-CTLA-4 therapy: enhancing efficacy while avoiding toxicity." Clinical Cancer Research, Oct. 1, 2013, 19(19):5261, 4 pages.
Marabelle et al., "Intratomoral immunization: a new paradigm for cancer therapy," Clinical Cancer Research, Apr. 1, 2014, 20(7):1747-56.
Marabelle et al., "Intratumoral immunotherapy: using the tumor as the remedy." Annals of Oncology, Dec. 1, 2017, 28:xii33-43, 11 pages.
Marabelle et al., "Starting the fight in the tumor: expert recommendations for the development of human intratumoral immunotherapy (HIT-IT)," Annals of Oncology, Nov. 1, 2018, 29(11):2163-74.
Mizukoshi et al., "Enhancement of tumor-associated antigen-specific T cell responses bv radiofrequency ablation of hepatocellular carcinoma," Hepatology, Apr. 2013, 57(4):1448-57.
Paiella et al., "Local ablative strategies for ductal pancreatic cancer (radiofrequency ablation, irreversible electroporation): a review," Gastroenterology Research and Practice, Oct. 2016, vol. 2016, 10 pages.
PCT International Preliminary Report on Patentability in International Application No. PCT/US2017/013486, dated Jul. 17, 2018, 33 pages.
PCT International Search Report and Written Opinion in International Application No. PCT/US2017/013486, dated May 19, 2017, 38 pages.
PCT International Search Report and Written Opinion in PCT Appln. No. PCT/US2019/066876, dated Jun. 2, 2020, 11 pages.
PRNewswire.com. "Image Guided Cancer Specialists Reports Successful Early Results from Cryoablation and Intra-tumoral Injection of Immunotherapy Drug Combination Yerivoy and Keytruda for the Treatment of Cancer," Feb. 3, 2015, retrieved Nov. 17, 2020 from URL <https://www.prnewswire.com/news-releases/image-guided-cancer-specialists-reports-successful-early-results-from-cryoablation-and-intra-tumoral-injection-of-immunotherapy-drug-combination-yerivoy-and-keytruda-for-the-treatment-of-cancer-300029347.html>, 3 pages.
Rosenberg et al., "Image guided cryoablation of cancer with intratumoral injection of anti-CTLA-4 and PD-1 immune check-point inhibitors," Journal for ImmunoTherapy of Cancer, Dec. 2015, 3(2):1-4.
Royal, et al., "Phase 2 trial of single agent ipilimumab (anti-CLTA-4) for locally advanced or metastatic pancreatic adenocarcinoma." J. Immunother., Oct. 2010, 33(8):828-833
Shi et al., "PD-1 blockade boosts radiofrequency ablation-elicited adaptive immune responses against tumor," Clinical Cancer Research, Mar. 1, 2016, 22(5):1173-84.
Sidana, "Cancer immminotherapy using tumor cryoablation," Immunotherapy, Jan. 2014, 6(1):85-93.
Somasundaram et al., "Nivolumab in Combination with Ipilimumab for the Treatment of Melanoma. Expert Review of Anti-Cancer Therapy," 15(10):1-13, dated Oct. 2015.
Waitz et al., "CTLA-4 blockade synergizes with cryoablation to mediate tumor rejection." Oncoimmunology, July 1, 2012, 1(4):544-6.
Wang et al., "In Vitro Characterization of the Anti-PD-1 Antibody Nivolumab, BMS-936558, and In Vivo Toxicology in Non-Human Primates," Cancer Immunology Research 2(9):846-856, dated May 28, 2014.

(56) References Cited

OTHER PUBLICATIONS

Williams, "The Immunotherapy Revolution: The Best New Hope For Saving Cancer Patients' Lives," Gatekeeper Press, Nov. 30, 2019, 115 pages.

Woolley et al., "Effect of Freezing Parameters (Freeze Cycle and Thaw Process) on Tissue Destruction Following Renal Cryoablation," Journal of Endourology 16(7):519-522, dated Sep. 2002.

Yu et al., "Treatment of osteosarcoma with microwave thermal ablation to induce immunogenic cell death," Oncotarget, Aug. 2014, 5(15):6526-39.

Zhou et al., "Structural repertoire of HIV-1-neutralizing antibodies targeting the CD4 supersite in 14 donors," Cell, Jun. 4, 2015, 161(6):1280-92.

\* cited by examiner

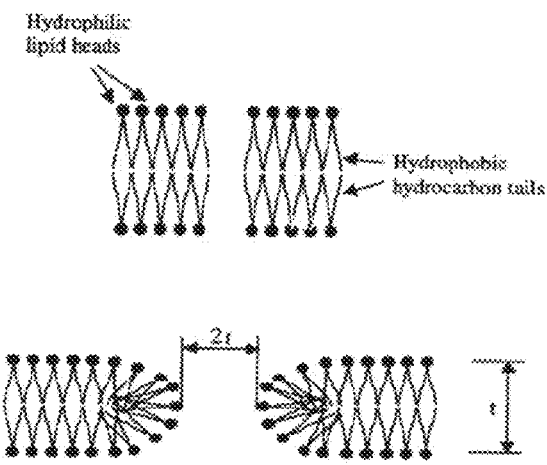
Fig. 1 - Prior Art
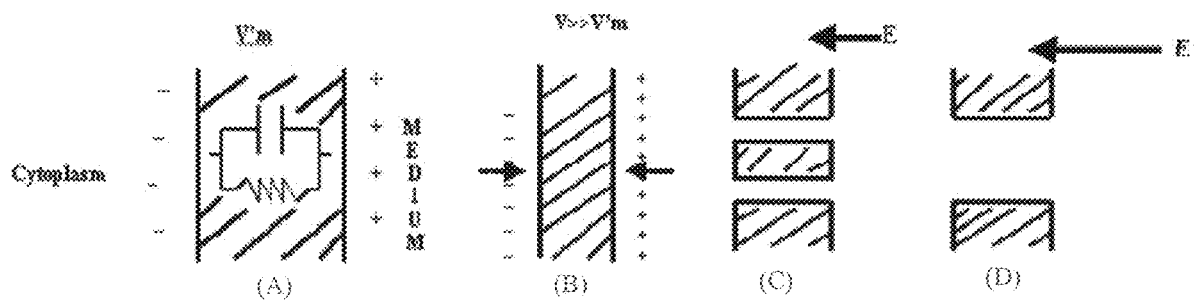
Fig. 2 - Prior Art

RADIO-FREQUENCY ELECTRICAL MEMBRANE BREAKDOWN FOR THE TREATMENT OF HIGH RISK AND RECURRENT PROSTATE CANCER, UNRESECTABLE PANCREATIC CANCER, TUMORS OF THE BREAST, MELANOMA OR OTHER SKIN MALIGNANCIES, SARCOMA, SOFT TISSUE TUMORS, DUCTAL CARCINOMA, NEOPLASIA, AND INTRA AND EXTRA LUMINAL ABNORMAL TISSUE

CROSS-REFERENCE TO RELATED APPLICATIONS

The present invention is a continuation-in-part of U.S. patent application Ser. No. 14/451,333, filed Aug. 4, 2014.

BACKGROUND OF THE INVENTION

1. Field of the Invention

The present invention relates generally to medical devices and treatment methods, and more particularly, to a device and method of treating prostate cancer by ablating cancerous tissue using applied electric fields.

2. Description of the Background

Cancer is not one single disease but rather a group of diseases with common characteristics that often result in sustained cell proliferation, reduced or delayed cell mortality, cooption of bodily angiogenesis and metabolic processes and evasion of bodily immune response which results in undesirable soft tissue growths called neoplasms or, more commonly, tumors. Removal or destruction of this aberrant tissue is a goal of many cancer treatment methods and modalities. Surgical tumor excision is one method of accomplishing this goal. Tissue ablation is another, minimally invasive method of destroying undesirable tissue in the body, and has been generally divided into thermal and non-thermal ablation technologies. Thermal ablation encompasses both the addition and removal of heat to destroy undesirable cells. Cryoablation is a well established technique that kills cells by freezing of the extracellular compartment resulting in cell dehydration beginning at −15 C and by intracellular ice formation causing membrane rupture occurring at colder temperatures. Because cryoablative techniques can rupture the cell membrane without denaturing cell proteins under certain conditions, such techniques have the additional ability to stimulate an antitumor immune response in the patient.

Heat based techniques are also well established for ablation of both cancerous and non cancerous tissues and include radio-frequency (RF) thermal, microwave and high intensity focused ultrasound ablation which raise localized tissue temperatures well above the body's normal 37° C. These methods use various techniques to apply energy to the target cells to raise interstitial temperature. For example, RF thermal ablation uses a high frequency electric field to induce vibrations in the cell membrane that are converted to heat by friction. Cell death occurs in as little as 30 seconds once die cell temperature reaches 50° C. and increases as the temperature rises. At 60° C. cell death is instantaneous. If the intracellular temperature rises to between about 60 and 95° C., the mechanisms involved in cell death include cellular desiccation and protein coagulation. When the intracellular temperature reaches 100° C., cellular vaporization occurs as intracellular water boils to steam. In the context of tissue ablation, cell temperatures not exceeding 50° C. are not considered clinically significant. Because cellular proteins are denatured by the heat of thermal ablation techniques, they are not available to stimulate a specific immune response as they may be with cryoablation. Both heat based and cryoablation techniques suffer from the drawback, that they have little or no ability to spare normal structures in the treatment zone and so can be contraindicated based on tumor location or lead to complications from collateral injury. Mapping biopsies, guided by ultrasound and augmented by information from sophisticated imaging such as MRI, can allow exact targeting of a patient's cancer to enable a targeted focal ablation method.

Non thermal ablation techniques include electrochemotherapy and irreversible electroporation which although quite distinct from one another, each rely on the phenomenon of electroporation. With reference to FIG. 1, electroporation refers to the fact that the plasma membrane of a cell exposed to high voltage pulsed electric fields within certain parameters, becomes temporarily permeable due to destabilization of the lipid bilayer and the formation of pores P. The cell plasma membrane consists of a lipid bilayer with a thickness t of approximately 5 nm. With reference to FIG. 2(A), the membrane acts as a nonconducting, dielectric barrier forming, in essence, a capacitor. Physiological conditions produce a natural electric potential difference due to charge separation across the membrane between the inside and outside of the cell even in the absence of an applied electric field. This resting transmembrane potential V'm ranges from 40 mv for adipose cells to 85 mv for skeletal muscle cells and 90 mv cardiac muscle cells and can vary by cell size and ion concentration among other things.

With continued reference to FIGS. 2(B)-2(D), exposure of a cell to an externally applied electric field E induces an additional voltage V across the membrane as long as the external field is present. The induced transmembrane voltage is proportional to the strength of the external electric field and the radius of the cell. Formation of transmembrane pores P in the membrane occurs if the cumulative resting and applied transmembrane potential exceeds the threshold voltage which may typically be between 200 mV and 1 V. Poration of the membrane is reversible if the transmembrane potential does not exceed the critical value such that the pore area is small in relation to the total membrane surface. In such reversible electroporation, the cell membrane recovers after the applied field is removed and the cell remains viable. Above a critical transmembrane potential and with longer exposure times, poration becomes irreversible leading to eventual cell death due an influx of extracellular ions resulting in loss of homeostasis and subsequent apoptosis. Pathology after irreversible electroporation of a ceil does not show structural or cellular changes until 24 hours after field exposure except in certain very limited tissue types. However, in all cases the mechanism of cellular destruction and death by IRE is apoptotic which requires considerable time to pass and is not visible pathologically in a time frame to be clinically useful in determining the efficacy of IRE treatment which is an important clinical drawback to the method.

Developed in the early 1990's, electrochemotherapy combines the physical effect of reversible cell membrane poration with administration, of chemotherapy drugs such as cisplatin and bleomycin. By temporarily increasing the cell membrane permeability, uptake of non-permeant or poorly permeant chemotherapeutic drugs is greatly enhanced. After the electric field is discontinued, the pores close and the drug molecules are retained inside the target cells without significant damage to the exposed cells. This approach to chemotherapy grew out of earlier research developing electroporation as a technique for transfection of genes and DNA molecules for therapeutic effect. In this context, irreversible electroporation leading to cell death was viewed as a failure in as much as the treated cells did not survive to realize the modification as intended.

Irreversible electroporation (IRE) as an ablation method grew out of the realization that the "failure" to achieve reversible electroporation could be utilized to selectively kill undesired tissue. IRE effectively kills a predictable treatment area without the drawbacks of thermal ablation methods that destroy adjacent vascular and collagen structures. During a typical IRE treatment, one to three pairs of electrodes are placed in or around the tumor. Electrical pulses carefully chosen to induce an electrical field strength above the critical transmembrane potential are delivered in groups of 10, usually for nine cycles. Each 10-pulse cycle takes about one second, and the electrodes pause briefly before starting the next cycle. As described in U.S. Pat. No. 8,048,067 to Rubinsky, et. al and U.S. patent application Ser. No. 13/332,133 by Arena, et al. which are incorporated here by reference, the field strength and pulse characteristics are chosen to provide the necessary field strength for IRE but without inducing thermal effects as with RP thermal ablation.

However, the DC pulses used in currently available IRE methods and devices have characteristics that can limit their use or add risks for the patient because current methods and devices create severe muscle contraction during treatment. This is a significant disadvantage because it requires that a patient be placed and supported under general anesthesia with neuromuscular blockade in order for the procedure to be carried out, and this carries with it additional substantial inherent patient risks and costs. Moreover, since even relatively small muscular contractions can disrupt the proper placement of IRE electrodes, the efficacy of each additional pulse train used in a therapy regimen may be compromised without even being noticed during the treatment session.

In addition, because cells ablated by IRE methods undergo apoptotic death without membrane rupture their ability to induce a supplemental immune response as observed with cryoablation is impaired. When used as the sole ablative tool in a treatment protocol, IRE's inability to induce a supplemental immune response is a substantial limitation to its therapeutic benefit for patients. On the other hand, cryoablation is limited by significant clinical disadvantages arising from the extreme cold and its capacity to destroy nearby critical healthy structures.

For the treatment of prostate cancer, focal therapies such as focal cryoablation are gaining acceptance among physicians as a middle ground between "watchful waiting" with no immediate therapeutic action and whole gland therapies, such as radical prostatectomy or radiation therapy, which are often associated with significant morbidities, particularly in the setting of high risk prostate cancer, and which often are not even clinically useful in cases of recurrent disease. At the present time, all methods for carrying out focal therapy involve technologies that require full operating room capabilities, or imaging capabilities such as MRI, both of which are very expensive and in relatively limited supply. As an additional downside, high risk prostate cancers, such as cancers involving High Gleason score, high Prostate-Specific Antigen (PSA), or high grade prostate cancer, have high recurrence rates, approaching 40% according to some studies, both locally and distantly when treated with conventional therapies such as radical prostatectomy and radiation therapy.

Meanwhile, very important clinical advantages have been demonstrated by the instant inventors in cases high risk prostate cancer patients treated with focal cryoablation. Their studies have demonstrated a dramatic improvement in overall long term survival, which they attribute to the immunological effects of focal cryoablation. This is also the case for patients who have failed a primary treatment such as radiation therapy or radical prostatectomy and who have locally recurrent disease that is treated using focal cryoablation. While these advantages are considerable, successful focal cryoablation is greatly dependent on the skill of the physician applying it and the individual techniques and methods they use. Prior art methods require substantial time and particular treatment procedures and repeated freeze and thaw cycles around very specific parameters in order to be effective and avoid damage to nearby structures.

What is needed is a minimally invasive tissue ablation technology that can avoid damaging healthy tissue while exposing cellular contents without denaturing such cellular contents so that they can trigger a clinically useful immune response.

In addition, an ablation method that can be accurately targeted at previously identified unwanted tissue, and that spares tissue structure outside of the focal treatment area, would be advantageous.

It would also be advantageous to provide a system and method for carrying out this treatment in a medical setting such as a physician's office or outpatient setting under local anesthesia, using a method that does not require general anesthesia or a neuromuscular blockade.

SUMMARY OF THE INVENTION

It is, therefore, an object of the present invention to provide a method for the treatment of prostate cancer in an outpatient or doctor's office setting via tissue ablation using electrical pulses which causes immediate cell death through the mechanism of complete break down of the membrane of the prostate cancer cell.

It is another object of the present invention to provide such a treatment method that does not require the administration of general anesthesia or a neuromuscular blockade to the patient.

The present invention is an imaging, guidance, planning and treatment system integrated into a single unit or assembly of components, and a method far using same, that can be safely and effectively deployed to treat prostate cancer in all medical settings, including in a physician's office or in an outpatient setting. The system utilizes the novel process of Radio-Frequency Electrical Membrane Breakdown ("EMB" or "RFEMB") to destroy the cellular membranes of unwanted or cancerous tissue without denaturing the intracellular contents of the cells comprising the tissue, thereby exposing tumor antigens and other intra-cellular components which can have an immunologic effect on local or distant cancerous tissue, with or without the addition of immunologic adjuvant drugs.

The use of EMB to achieve focal tumor ablation with an enhanced immunologic effect on surrounding cancerous tissue is disclosed in U.S. patent application Ser. No. 14/451,333 and International Patent Application No. PCT/US14/68774, which are both fully incorporated herein by reference.

EMB is the application of an external oscillating electric field to cause vibration and flexing of the cell membrane, which results in a dramatic and immediate mechanical tearing, disintegration and/or rupturing of the cell membrane. Unlike the IRE process, in which nano-pores are created in the cell membrane but through which little or no content of the cell is released, EMB completely tears open the cell membrane such that the entire contents of the cell are expelled into the extracellular fluid, and internal components of the cell membrane itself are exposed. EMB achieves this effect by applying specifically configured electric field profiles, comprising significantly higher energy levels (as much as 100 times greater) as compared to the IRE process, to directly and completely disintegrate the cell membrane rather than to electroporate the cell membrane. Such electric field profiles are not possible using currently available IRE equipment and protocols. The inability of current IRE methods and energy protocols to deliver the energy necessary to cause EMB explains why IRE treated specimens have never shown the pathologic characteristics of EMB treated specimens, and is a critical reason why EMB had not until now been recognized as an alternative method of cell destruction.

The system according to the present invention comprises a software and hardware system, and method for using the same, for detecting and measuring a mass of cancerous tissue in the prostate of a patient, for designing an EMB treatment protocol to ablate said cancerous mass, and for applying said EMB treatment protocol in an outpatient or doctor's office setting. The system includes an EMB pulse generator 16, one or more EMB treatment probes 20, one or more trackable biopsy needles 200 and one or more temperature probes 22. The system further employs a software-hardware controller unit (SHCU) operatively connected to said generator 16, probes 20, biopsy needles 200 and temperature probe(s) 22, along with one or more optional devices such as trackable anesthesia needles 300, endoscopic imaging scanners, ultrasound scanners, and/or other imaging devices or energy sources, and operating software for controlling the operation of each of these hardware devices.

BRIEF DESCRIPTION OF THE DRAWINGS

FIG. 1 is a diagram of a cell membrane pore.

FIG. 2 is a diagram of a cell membrane pore formation by a prior art method.

DETAILED DESCRIPTION

In general, the software-hardware controller unit (SHCU) operating the proprietary office based prostate cancer treatment system software according to the present invention facilitates the treatment of prostate cancer by directing the placement of EMB treatment probe(s) 20, biopsy needle(s) 200 and, optionally, anesthesia needle(s) 300, and by delivering electric pulses designed to cause EMB within the cancerous tissue to EMB treatment probe(s) 20, all while the entire process may be monitored in real time via one or more two- or three-dimensional imaging devices and via one or more biopsy samples taken at strategic locations to measure cell death. The system is such that the treatment may be performed by a physician under the guidance of the software, or may be performed completely automatically, from the process of imaging the treatment area to the process of placing one or more probes using robotic arms operatively connected to the SHCU to the process of delivering electric pulses and monitoring the results of same. Specific components of the invention will now be described in greater detail.

EMB Pulse Generator 16

Figure 9:
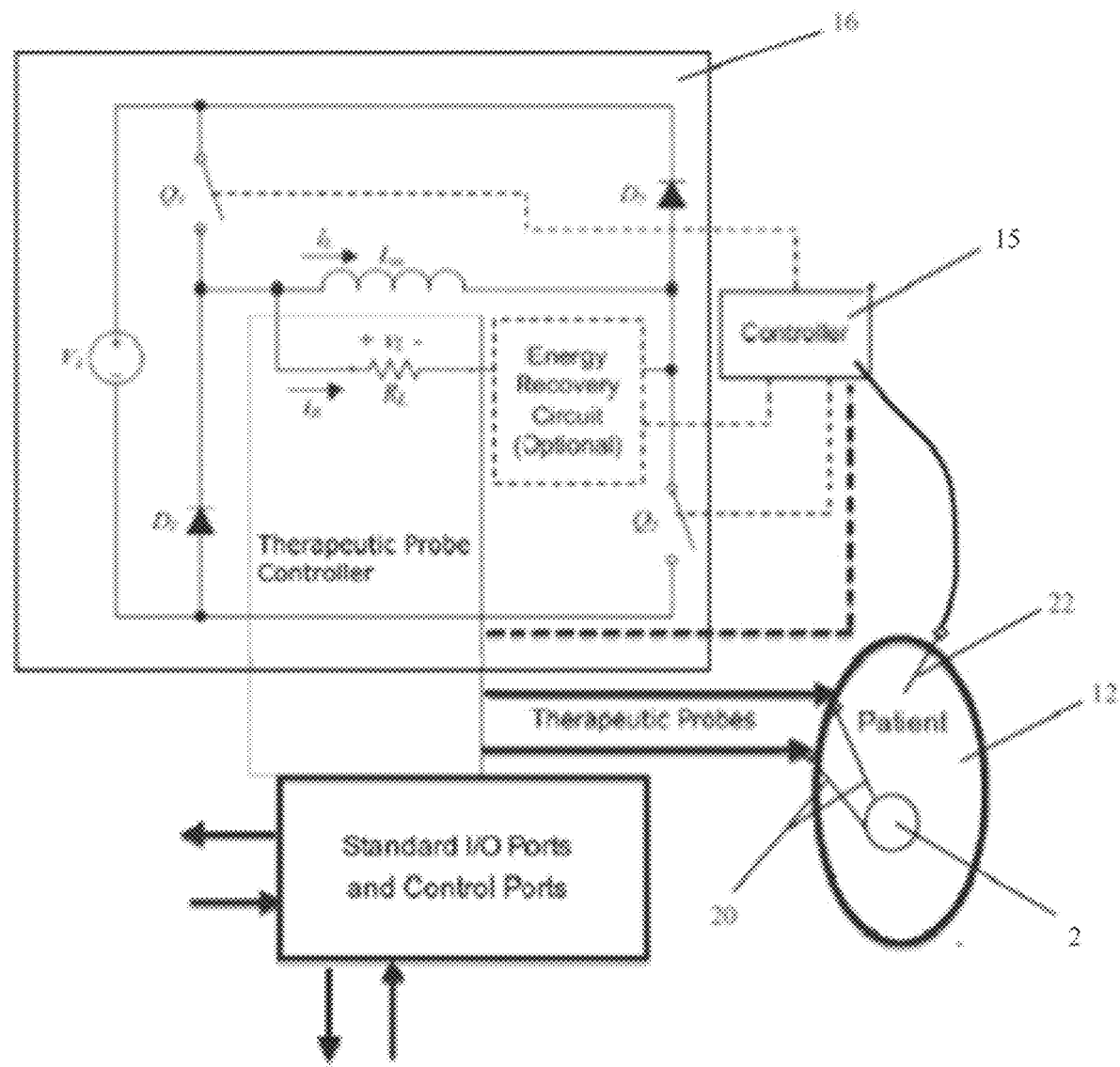
FIG. 9 is a schematic diagram of a pulse generation and delivery system for application of the method of the present invention.

FIG. 9 is a schematic diagram of a system, for generation of the electric field necessary to induce EMB of cells 2 within a patient 12. The system includes the EMB pulse generator 16 operatively coupled to Software Hardware Control Unit (SHCU) 14 for controlling generation and delivery to the EMB treatment probes 20 (two are shown) of the electrical pulses necessary to generate an appropriate electric field to achieve EMB. FIG. 9 also depicts optional onboard controller 15 which is preferably the point of interface between EMB pulse generator 16 and SHCU 14. Thus, onboard controller 15 may perform functions such as accepting triggering data from SHCU 14 for relay to pulse generator 16 and providing feedback to SHCU regarding the functioning of the pulse generator 16. The EMB treatment probes 20 (described in greater detail below) are placed in proximity to the soft tissue or cancerous cells 2 which are intended to be ablated through the process of EMB and the bipolar pulses are shaped, designed and applied to achieve that result in an optimal fashion. A temperature probe 22 may be provided for percutaneous temperature measurement and feedback to the controller of the temperature at, on or near the electrodes. The controller may preferably include an onboard digital processor and a memory and may be a general purpose computer system, programmable logic controller or similar digital logic control device. The controller is preferably configured to control the signal output characteristics of the signal generation including the voltage, frequency, shape, polarity and duration of pulses as well as the total number of pulses delivered in a pulse train and the duration of the inter pulse burst interval.

With continued reference to FIG. 9, the EMB protocol calls for a series of short and intense bi-polar electric pulses delivered from the pulse generator through one or more EMB treatment probes 20 inserted directly into, or placed around the target tissue 2. The bi-polar pulses generate an oscillating electric field between the electrodes that induce a similarly rapid and oscillating buildup of transmembrane potential across the cell membrane. The built up charge applies an oscillating and flexing force to the cellular membrane which upon reaching a critical value causes rupture of the membrane and spillage of the cellular content. Bipolar pulses are more lethal than monopolar pulses because the pulsed electric field causes movement of charged molecules in the cell membrane and reversal in the orientation or polarity of the electric field causes a corresponding change in the direction of movement of the charged molecules and of the forces acting on the cell. The added stresses that are placed on the cell membrane by alternating changes in the movement of charged molecules create additional internal and external changes that cause indentations, crevasses, rifts and irregular sudden tears in the cell membrane causing more extensive, diverse and random damage, and disintegration of the cell membrane.

Figure 4A:
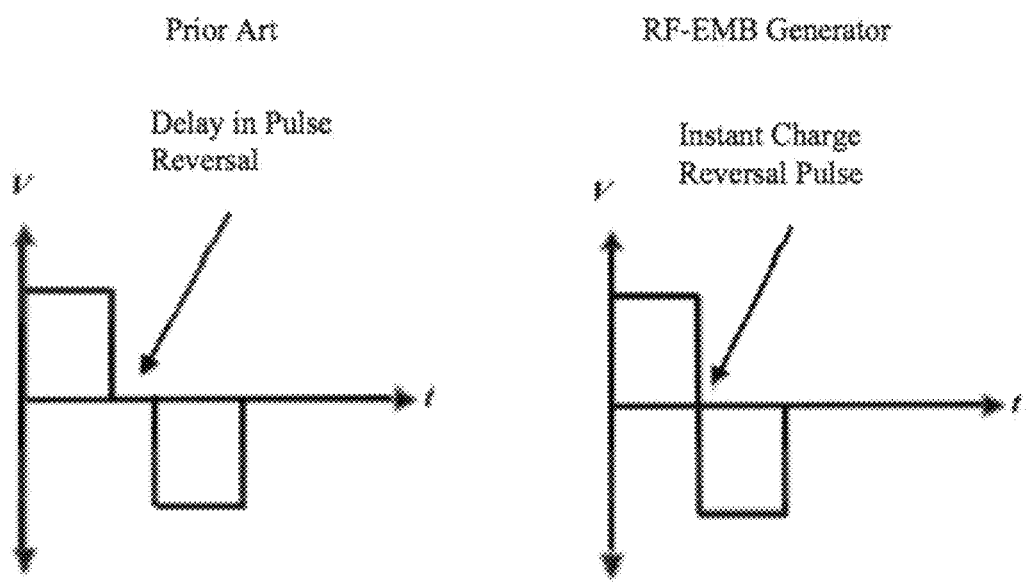
FIG. 4A is a comparison of a prior art charge reversal with an instant charge reversal according to the present invention.
Figure 4B:
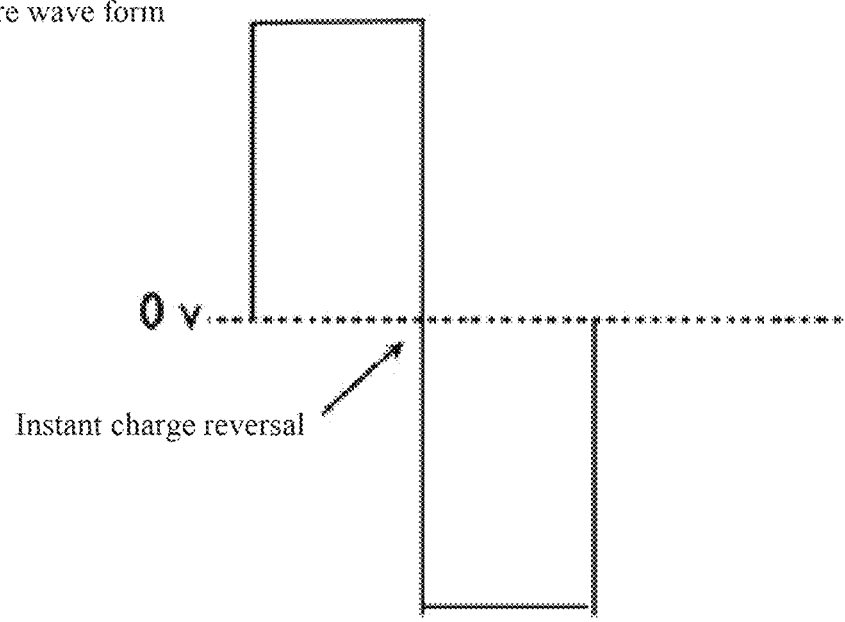
FIG. 4B is a square wave from instant charge reversal pulse according to the present invention.

With reference to FIG. 4B, in addition to being bi-polar, the preferred embodiment of electric pulses is one for which the voltage over time traces a square wave form and is characterized by instant charge reversal pulses (ICR). A square voltage wave form is one that maintains a substantially constant voltage of not less than 80% of peak voltage for the duration of the single polarity portion of the trace, except during the polarity transition. An instant charge reversal pulse is a pulse that is specifically designed to ensure that substantially no relaxation time is permitted between the positive and negative polarities of the bi-polar pulse (See FIG. 4A). That is, the polarity transition happens virtually instantaneously.

The destruction of dielectric cell membranes through the process of Electrical Membrane Breakdown is significantly more effective if the applied voltage pulse can transition from a positive to a negative polarity without delay in between. Instant charge reversal prevents rearrangement of induced surface charges resulting in a short state of tension and transient mechanical forces in the cells, the effects of which are amplified by large and abrupt force reversals. Alternating stress on the target cell that causes structural fatigue is thought to reduce the critical electric field strength required for EMB. The added structural fatigue inside and along the cell membrane results in or contributes to physical changes in the structure of the cell. These physical changes and defects appear in response to the force applied with the oscillating EMB protocol and approach dielectric membrane breakdown as the membrane position shifts in response to the oscillation, up to the point of total membrane rupture and catastrophic discharge. This can be analogized to fatigue or weakening of a material caused by progressive and localized structural damage that occurs when a material is subjected to cyclic loading, such as for example a metal paper clip that is subjected to repeated bending. The nominal maximum stress values that cause such damage may be much less than the strength of the material under ordinary conditions. The effectiveness of this waveform compared to other pulse waveforms can save up to ⅕ or ⅙ of the total energy requirement.

Figure 10:
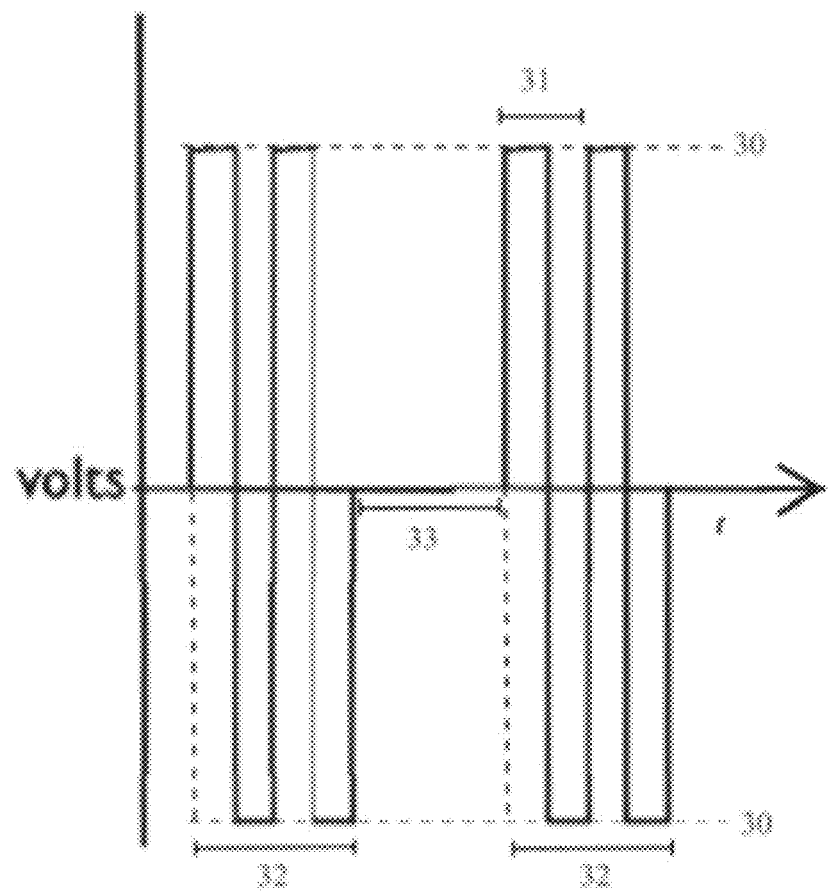
FIG. 10 is a diagram of the parameters of a partial pulse train according to the present invention.
Figure 11:
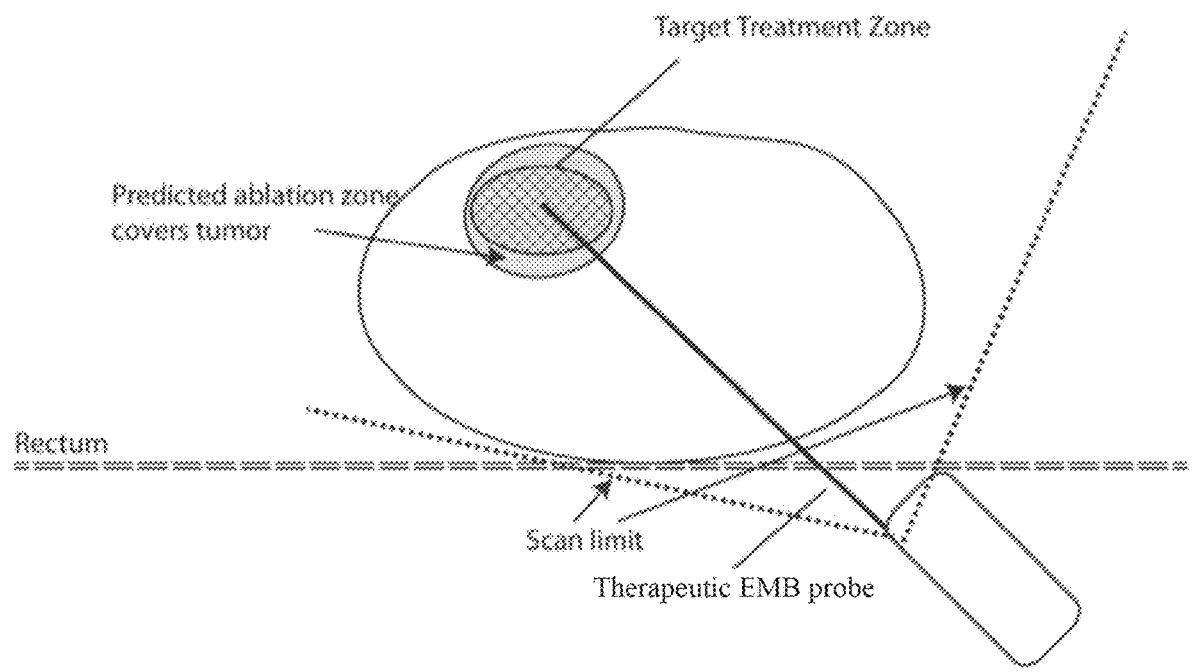
FIG. 11 is a schematic diagram depicting the target treatment area and Predicted Ablation Zone relative to a therapeutic EMB treatment probe 20 at the start of treatment delivery.

With reference to FIG. 10, another important characteristic of the applied electric field is the field strength (Volts/cm) which is a function of both the voltage 30 applied to the electrodes by the pulse generator 16 and the electrode spacing. Typical electrode spacing for a bi-polar, needle type probe might be 1 cm, while spacing between multiple needle probe electrodes can be selected by the surgeon and might typically be from 0.75 cm to 1.5 cm. A pulse generator for application of the present invention is capable of delivering up to a 10 kV potential. The actual applied field strength will vary over the course of a treatment to control circuit amperage which is the controlling factor in heat generation, and patient safety (preventing large unanticipated current flows as the tissue impedance falls during a treatment). Where voltage and thus field strength is limited by heating concerns, the duration of the treatment cycle may be extended to compensate for the diminished charge accumulation. Absent thermal considerations, a preferred field strength for EMB is in the range of 1,500 V/cm to 10,000 V/cm.

Figure 5:
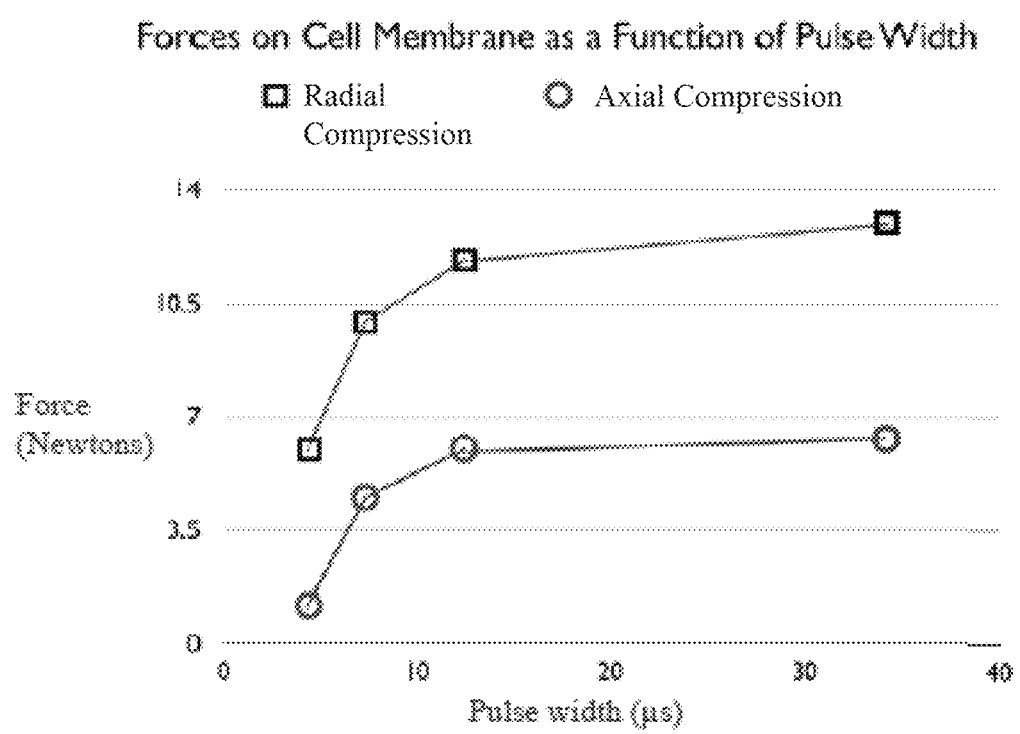
FIG. 5 is a diagram of the forces imposed on a cell membrane as a function of electric field pulse width according to the present invention.

With continued reference to FIG. 10, the frequency 31 of the electric signal supplied to the EMB treatment probes 20, and thus of the field polarity oscillations of the resulting electric field, influences the total energy imparted on the subject tissue and thus the efficacy of the treatment but are less critical than other characteristics. A preferred signal frequency is from 14.2 kHz to less than 500 kHz. The lower frequency bound imparts the maximum energy per cycle below which no further incremental energy deposition is achieved. With reference to FIG. 5, the upper frequency limit is set based on the observation that above 500 kHz, the polarity oscillations are too short to develop enough motive force on the cell membrane to induce the desired cell membrane distortion and movement. More specifically, at 500 kHz the duration of a single full cycle is 2 µs of which half is of positive polarity and half negative. When the duration of a single polarity approaches 1 µs there is insufficient time for charge to accumulate and motive force to develop on the membrane. Consequently, membrane movement is reduced or eliminated and EMB does not occur. In a more preferred embodiment the signal frequency is from 100 kHz to 450 kHz. Here the lower bound is determined by a desire to avoid the need for anesthesia or neuromuscular-blocking drugs to limit or avoid the muscle contraction stimulating effects of electrical signals applied to the body. The upper bound in this more preferred embodiment is suggested by the frequency of radiofrequency thermal ablation equipment already approved by the FDA, which has been deemed safe for therapeutic use in medical patients.

In addition, the energy profiles that are used to create EMB also avoid potentially serious patient risks from interference with cardiac sinus rhythm, as well as localized barotrauma, which can occur with other therapies.

EMB Treatment Probes 20

Figure 12A:
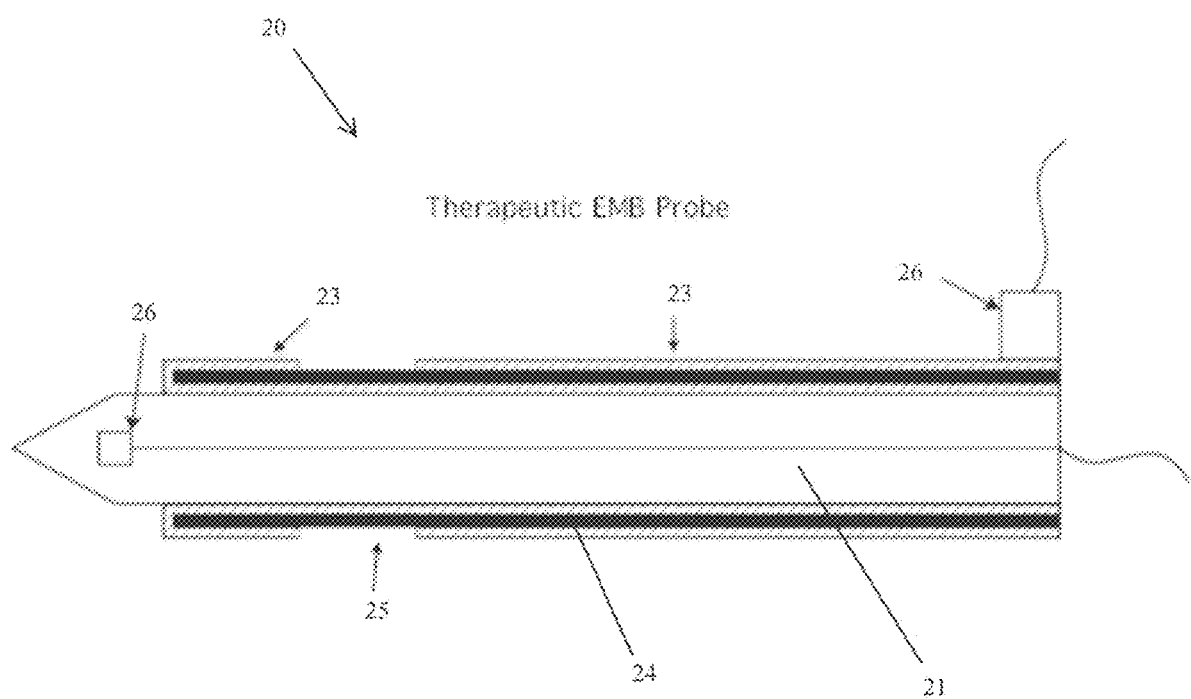
FIG. 12A is a schematic diagram of a therapeutic EMB treatment probe 20 according to one embodiment of the present invention.
Figure 12B:
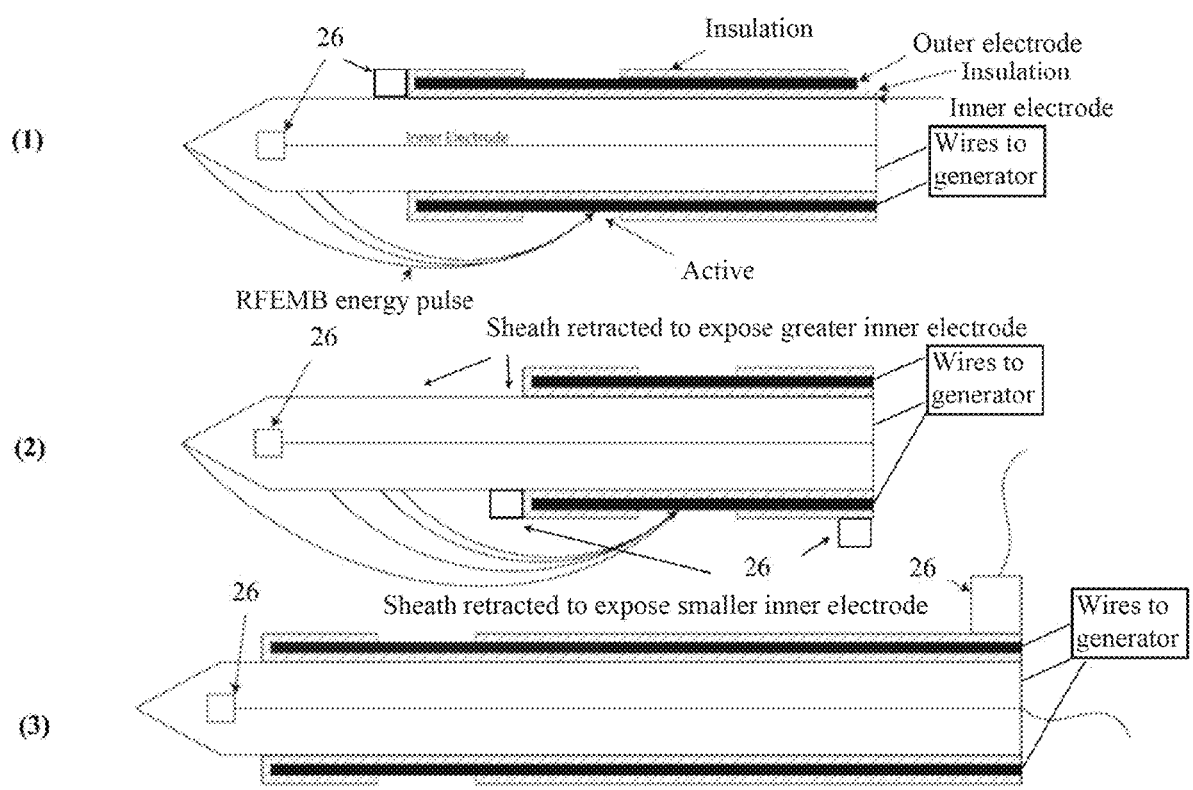
FIG. 12B is a composite schematic diagram (1, 2 and 3) of the therapeutic EMB treatment probe 20 of FIG. 12A showing insulating sheath 23 in various stages of retraction.
Figure 12C:
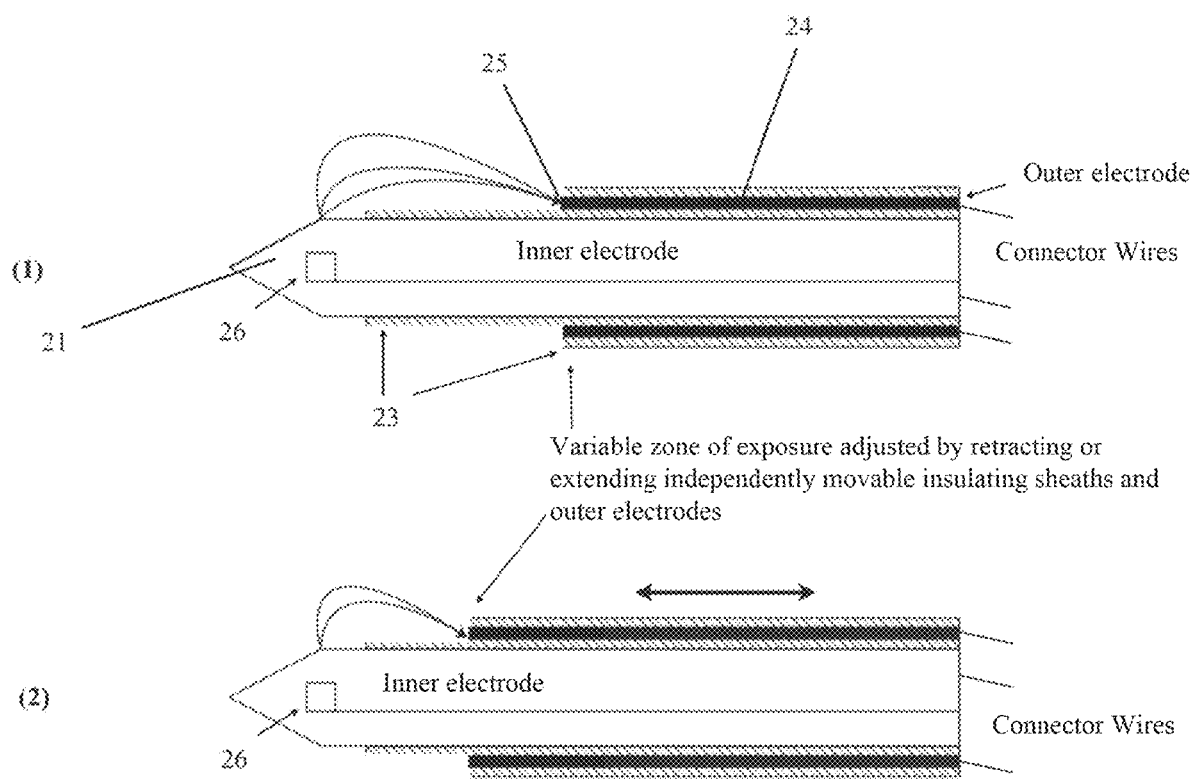
FIG. 12C is a composite schematic diagram (1 and 2) of a therapeutic FMB treatment probe 20 according to another embodiment of the present invention.
Figure 12D:
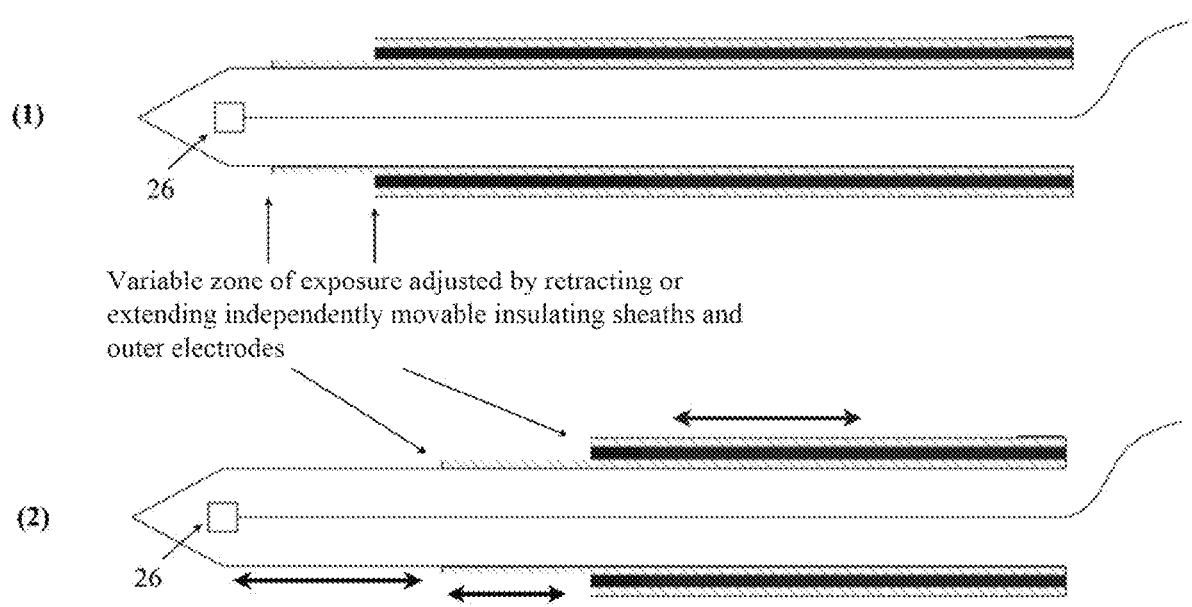
FIG. 12D is a composite schematic diagram (1 and 2) of the therapeutic EMB treatment probe 20 of FIG. 12C showing insulating sheath 23 in various stages of retraction.

FIGS. 12A-12B depict a first embodiment of a therapeutic EMB treatment probe 20. The core (or inner electrode) 21 of EMB treatment probe 20 is preferably a needle of gage 17-22 with a length of 5-25 cm, and may be solid or hollow. Core 21 is preferably made of an electrically conductive material, such as stainless steel, and may additionally comprise one or more coatings of another conductive material, such as copper or gold, on the surface thereof. As shown in FIGS. 12A-12D, in the instant embodiment, the core 21 of treatment probe 20 has a pointed tip, wherein the pointed shape may be a 3-sided trocar point or a beveled point; however, in other embodiments, the tip may be rounded or flat. Treatment probe 20 further comprises an outer electrode 24 covering core 21 on at least one side. In a preferred embodiment, outer electrode 24 is also a cylindrical member completely surrounding the diameter of core 21. An insulating sheath 23, made of an inert material compatible with bodily tissue, such as Teflon® or Mylar, is disposed around the exterior of core 21 and isolates core 21 from outer electrode 24. In this preferred embodiment, insulating sheath 23 is also a cylindrical body surrounding the entire diameter of core 21 and completely encapsulating outer electrode 24 except at active area 25, where outer electrode 24 is exposed directly to the treatment area. In an alternate embodiment, shown in FIGS. 12C-12D, insulating sheath 23 comprises two solid cylindrical sheaths wherein the outer sheath completely encapsulates the lateral area of outer electrode 24 and only the distal end of outer electrode 24 is exposed to the treatment area as active area 25. Insulating sheath 23 and outer electrode 24 are preferably movable as a unit along a lateral dimension of core 21 so that the surface area of core 21 that is exposed to the treatment area is adjustable, thus changing the size of the lesion created by the EMB pulses. FIGS. 12B(3) and 12C(2) depict insulating sheath 23 and outer electrode 24 advanced towards the pointed tip of core 21, defining a relatively small treatment area, while FIGS. 12B(2) and 120(1) depict insulating sheath 23 and outer electrode 24 retracted to define a relatively large treatment area. Electromagnetic (EM) sensors 26 on both core 21 and insulating sheath 23/outer electrode 24 member send information to the Software Hardware Controller Unit (SHCU) tor determining the relative positions of these two elements and thus the size of the treatment area, preferably in real time. EM sensors 26 may be a passive EM tracking sensor/field generator, such as the EM tracking sensor manufactured by Traxtal Inc. Alternatively, instead of utilizing EM sensors, EMB treatment probes 20 may be tracked in real time and guided using endoscopy, ultrasound or other imaging means known in the art.

One means for enabling the relative movement between core 21 and insulating sheath 23/outer electrode 24 member is to attach insulating sheath 23/outer electrode 24 member to a fixed member (i.e., a handle) at a distal end of probe 20 opposite the tip of core 21 by a screw mechanism, the turning of which would advance and retract the insulating sheath 23/outer electrode 24 member along the body of the core 21. Other means for achieving this functionality of EMB treatment probe 20 are known in the art.

One of conductive elements 21, 24 comprises a positive electrode, while the other comprises a negative electrode. Both core 21 and outer electrode 24 are connected to the EMB pulse generator 16 through insulated conductive wires, and which are capable of delivering therapeutic EMB pulsed radio frequency energy or biphasic pulsed electrical energy under sufficient conditions and with sufficient treatment parameters to achieve the destruction and disintegration of the membranes of prostate cancer cells, or unwanted tissue, through the process of EMB, as described in more detail above. The insulated connection wires may either be contained within the interior of EMB treatment probes 20 or on the surface thereof. However, EMB treatment probes 20 may also be designed to deliver thermal radio frequency energy treatment, if desired, as a complement to or instead of EMB treatment.

In another preferred embodiment of the present invention, EMB treatment probes 20 contain sensors of the type described by Laufer et al. in "Tissue Characterization Using Electrical Impedance Spectroscopy Data: A Linear Algebra Approach", Physiol. Meas. 33 (2012) 997-1013, to investigate tissue characteristics to determine cancerous from non-cancerous tissue. Alternatively, or in addition to sensors of the type described by Laufer, EMB treatment probes 20 may contain sensors to determine cellular content spillage as necessary to quantify cell death in the treatment area via EMB; one example of such a sensor is described by Miller et al. in "Integrated Carbon Fiber Electrodes Within Hollow Polymer Microneedles For Transdermal Electrochemical Sensing", Biomicrofluidics, 2011 Mar. 30; 5(1): 13415.

Alternatively, or in addition to the sensors described above, EMB treatment probes 20 may contain a thermocouple, such as a Type K-40AWG thermocouple with Polyimide Primary/Nylon Bond Coat insulation and a temperature range of −40 to +180 C, manufactured by Measurement Specialties. The lumen of the optional thermocouple may be located on EMB treatment probe 20 such that the temperature at the tip of the probe can be monitored and the energy delivery to probe 20 modified to maintain a desired temperature at the tip of probe 20.

Electrical membrane breakdown, unlike IRE or other thermal ablation techniques, causes immediate spillage of all intracellular components of the ruptured cells into an extracellular space and exposes the internal constituent parts of the cell membrane to the extracellular space. The intracellular components include cellular antigens and the internal constituent parts of the ceil membrane include antigens specific to the cell membrane which induce an immunologic response to destroy and remove this and like material in the body of the subject. Like material may be other material in the body of the subject having the same cellular antigens or cell membrane specific antigens at locations remote from the treatment site including metastatic tissue. The immunologic response can be enhanced by administration of drugs that increase the immunologic response process including drugs which block inhibition of the CTLA-4 inhibitory signal of cytotoxic lymphocytes or that binds to S100A9 and modulating regulatory myeloid cell functions.

Figure 17:
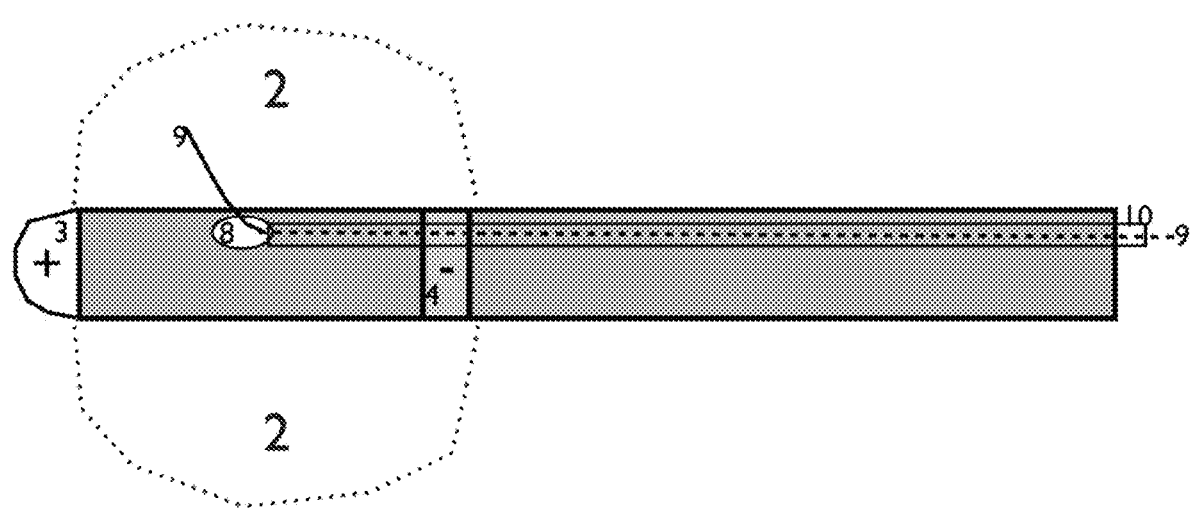
FIG. 17 is a schematic diagram depicting the positioning of a therapeutic EMB treatment probe 20 comprising a side port 8 for exposure of needle 9 according to another embodiment of the present invention proximate the treatment area 2.

Thus, alternatively or in addition to the sensors described above, EMB treatment probes 20 may have a hollow interior defined by an inner lumen 10 of sufficient diameter to accommodate a spinal needle 9 of one or more standard gauges to be inserted there through for the injection of adjuvant immunotherapy type drugs into the lesion formed by EMB treatment to enhance the immunologic response of said treatment (see FIG. 17). Alternatively, the inner lumen 10 may be sized to allow for the injection of biochemical or biophysical nano-materials there through into the EMB lesion to enhance the efficacy of the local ablative effect, or the immunologic response and effect of the EMB treatment, or to allow injection of reparative growth stimulating drugs, chemicals or materials. A lumen 10 of the type described herein may also advantageously allow the collection and removal of tissue or infra-cellular components from the treatment area or nearby vicinity. This functionality may take the place of the trackable biopsy needle 200 described in more detail below, and can be used for such purposes before, during or after the application of EMB pulses from the EMB treatment probe 20.

Figure 19:
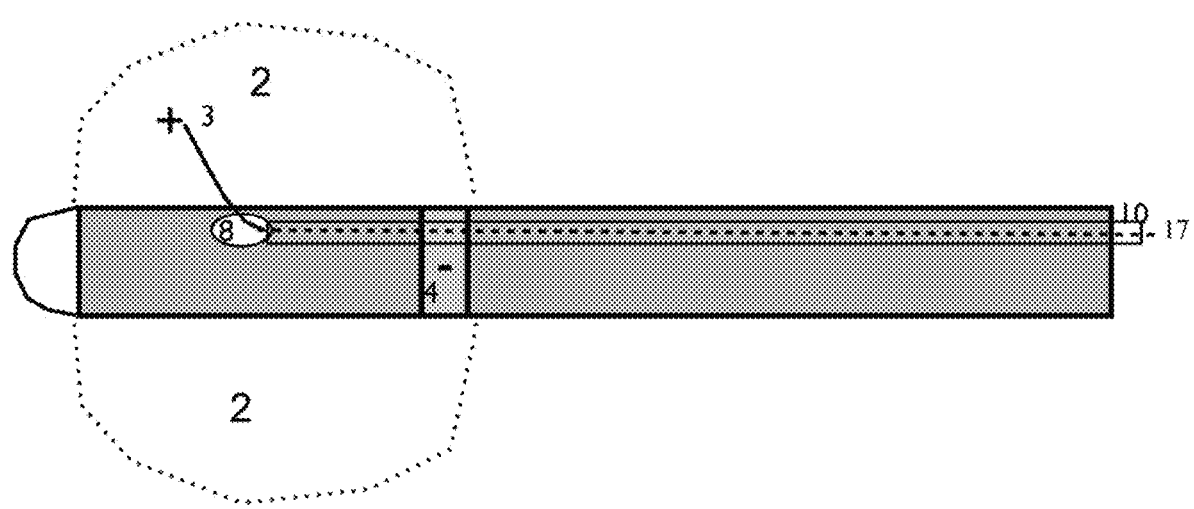
FIG. 19 is a schematic diagram depicting the positioning of a therapeutic EMB treatment probe 20 comprising a side port 8 for exposure of electrode-bearing needle 17 according to another embodiment of the present invention proximate the treatment area 2.

In an alternative embodiment of EMB treatment probes 20, one of either the positive (+) 3 or negative (−) 4 electrodes is on an outer surface of EMB treatment probe 20, while the other polarity of electrode is placed on the tip of a curved needle 17 inserted through a lumen 10 in the interior of core 21. Except for active surface 25 and a side hole 8, through which needle 17 may exit lumen 10, insulating sheath 23 may completely envelope probe 20 to isolate the two electrodes (see FIG. 19).

Figure 21:
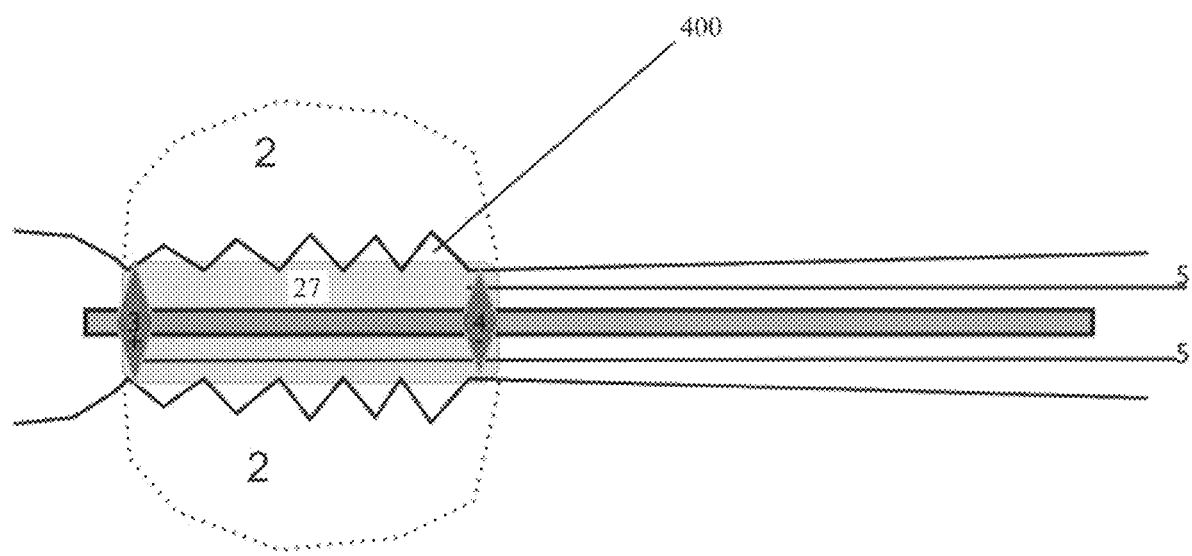
FIG. 21 is a schematic diagram depicting the positioning of a therapeutic EMB treatment probe 20 comprising an expandable stabilizing balloon 27 according to another embodiment of the present invention inside a cavity 400 in the human body.
Figure 22:
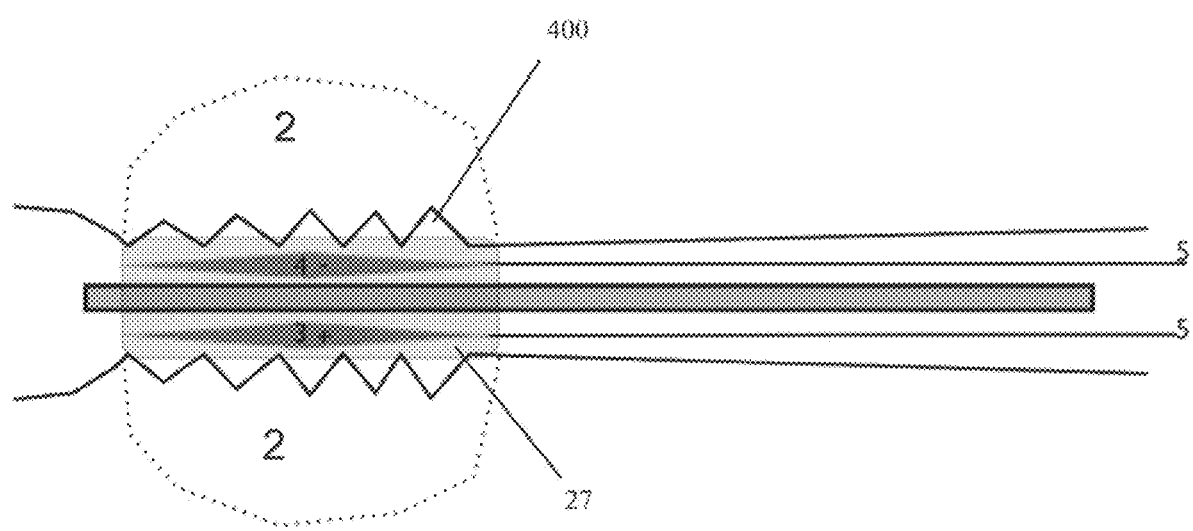
FIG. 22 is a schematic diagram depicting the positioning of a therapeutic EMB treatment probe 20 comprising an expandable electrode-hearing balloon 27 according to another embodiment of the present invention inside a cavity 400 in the human body.

In yet another alternative embodiment of EMB treatment probes 20, unipolar or bipolar electrodes are placed on an expandable balloon 27, the inflation of which may be controlled by the SHCU via a pneumatic motor or air pump, etc. In this embodiment, when the balloon 27 is placed inside a cavity 400 in the human body (proximate a designated treatment area) and inflated, the electrodes on the balloon's surface are forced against the wall of the cavity 400 to provide a path for current to flow between the positive and negative electrodes (see FIG. 21). The positive and negative electrodes can have different configurations on the balloon 27, i.e., they may be arranged horizontally around the circumference of the balloon 27 as in FIG. 21, or longitudinally along the long axis of the balloon as in FIG. 22. In some embodiments, more than one each of positive and negative electrodes may be arranged on a single balloon.

Figure 23:
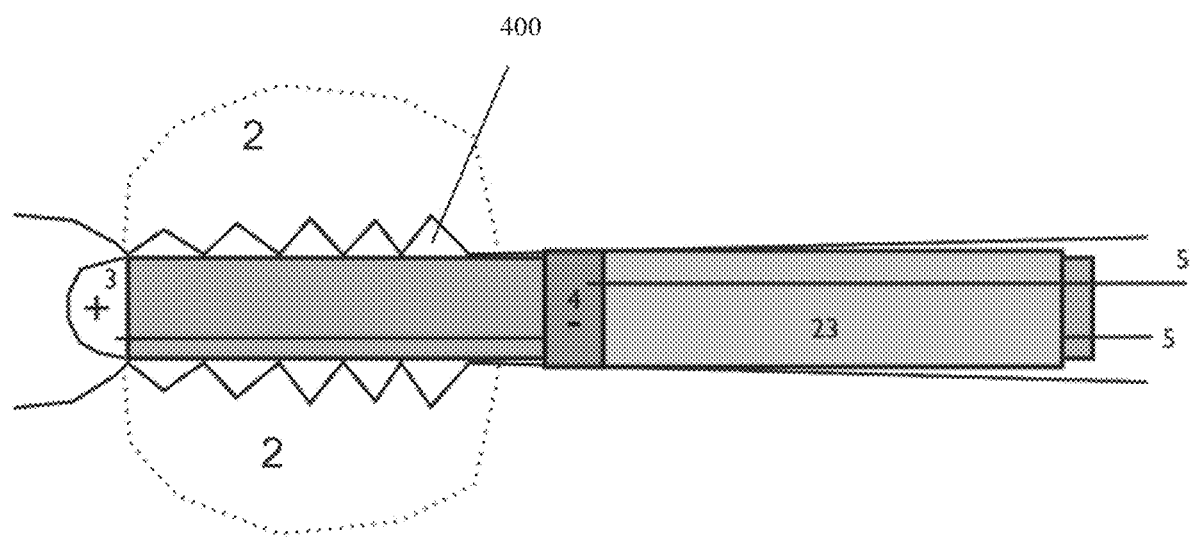
FIG. 23 is a schematic diagram depicting the positioning of a therapeutic EMB treatment probe 20 according to another embodiment of the present invention inside a cavity 400 in the human body.

In another embodiment one electrode is on the end of a sheath through which the EMB treatment probe 20 is placed. By moving the catheter various distances from the end of the sheath, various distances between the electrodes can be accomplished thus changing the size and shape of the treatment zone (see FIG. 23).

Figure 20:
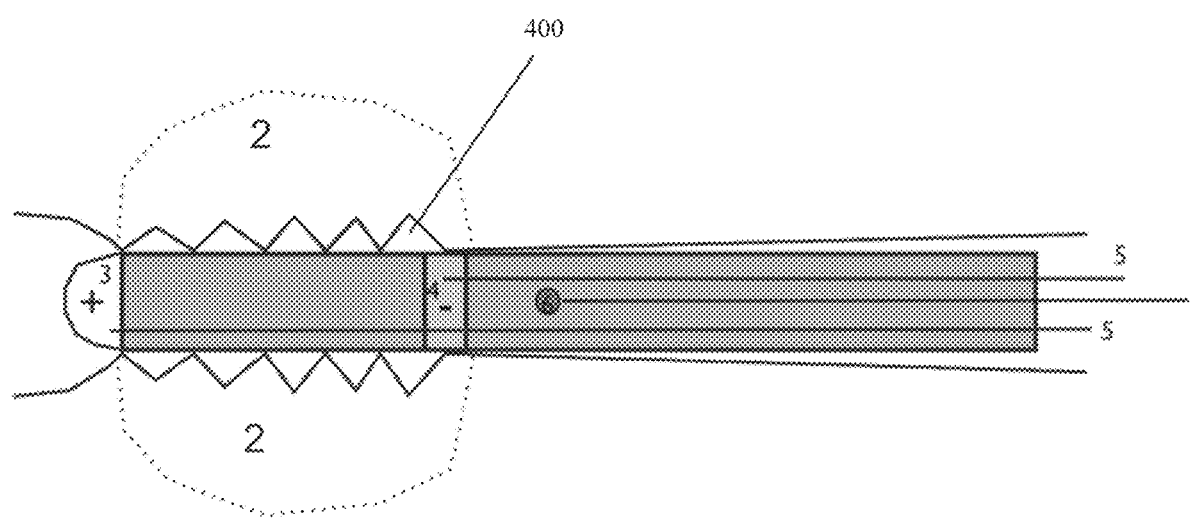
FIG. 20 is a schematic diagram depicting the positioning of a therapeutic EMB treatment probe 20 according to another embodiment of the present invention inside a cavity 400 in the human body.

In certain embodiments of the present invention, the EMB treatment probe 20 is inserted into the treatment area through a catheter inserted through the urethra for treatment of a cancerous mass 2 proximate the peri-urethral prostatic tissue (see FIG. 20). Optionally, the catheter may comprise a non-electrode-containing balloon that is otherwise of the general type described above on its distal end, such that when the balloon (not shown) is inflated, the catheter and EMB treatment probe 20 are anchored within the treatment area for prostate cancer by a friction fit of the balloon in the bladder neck. In other embodiments, EMB treatment probe 20 is made contiguous with and/or held within a catheter for ease of insertion of EMB probe 20 into the treatment area. A catheter for this purpose may be a Foley-type catheter, sized between 10 French to 20 French and made of silicone, latex or any other biocompatible, flexible material. Alternatively, a catheter through which EMB probes 20 are inserted may serve as one of a pair of bipolar electrodes, while the EMB treatment probe 20 is placed directly within the tissue of the prostate to serve as the other electrode.

Figure 18:
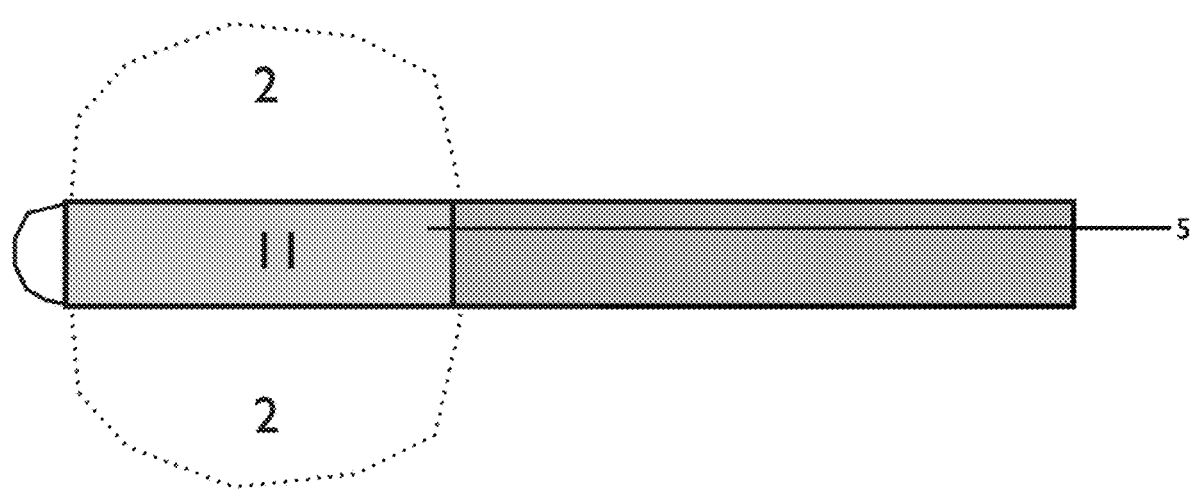
FIG. 18 is a schematic diagram depicting the positioning of a therapeutic EMB treatment probe 20 comprising a unipolar electrode 11 according to another embodiment of the present invention proximate the treatment area 2.
Figure 24:
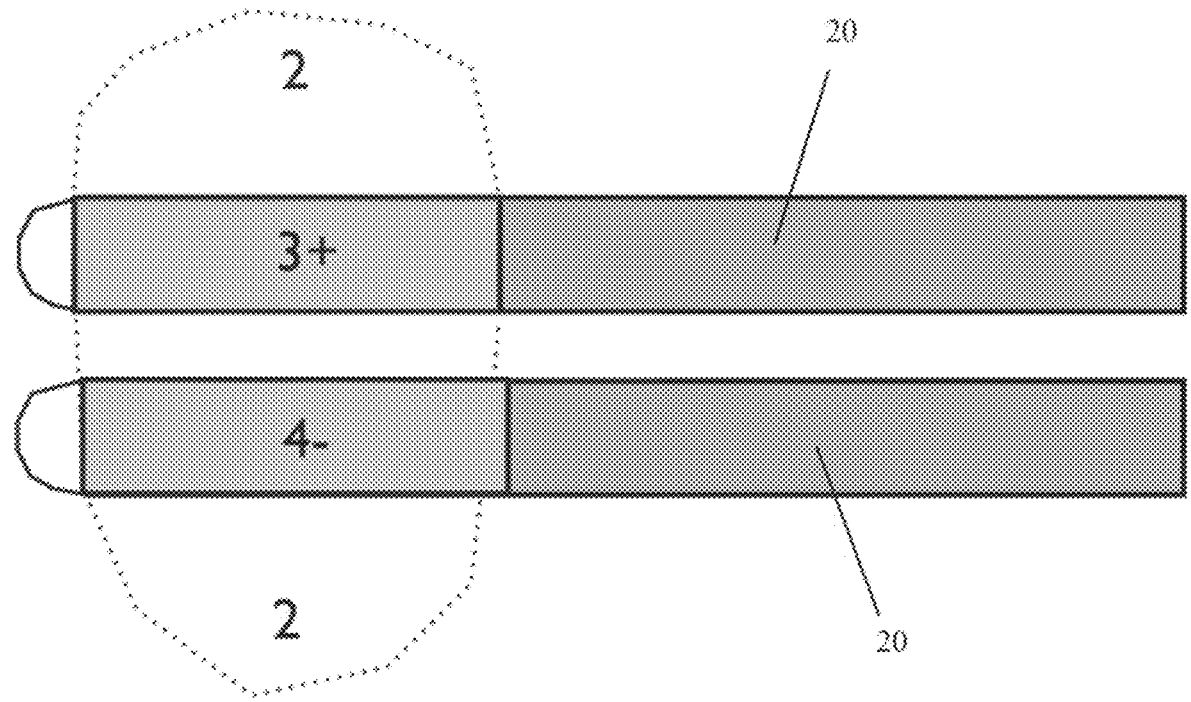
FIG. 24 is a schematic diagram depicting the use of two therapeutic EMB treatment probes 20 for delivery of EMB treatment.

One of ordinary skill in the art will understand that the EMB treatment probe(s) 20 may take various forms provided that they are still capable of delivering EMB pulses from the EMB pulse generator 16 of the type, duration, etc. described above. For example, the EMB treatment probes 20 have been described herein as a rigid assembly, but may also be semi-rigid assembly with formable, pliable and/or deformable components. As another example, EMB treatment probes 20 may be unipolar 11 (see FIG. 18) and used with an indifferent electrode placed on a remote location from the area of treatment (see FIG. 18). In yet another embodiment, two EMB treatment probes 20 may be used, wherein each probe has one each of a positive and negative electrode (See FIG. 24).

It will also be understood that, instead of a EMB treatment probe having a lumen capable of providing a delivery path for immunologic response enhancing drags, such drugs may be administered by any means, including without limitation, intravenously, orally or intramuscularly and may further be injected directly into or adjacent to the target soft tissue immediately before or after applying the EMB electric field. Such immunologic response enhancing drug may be comprised also of autologous dendritic cells.

Trackable Biopsy Needles 200

Unlike irreversible electroporation, electrical membrane breakdown EMB causes immediate visually observable tissue changes which show cellular membrane destruction and immediate cell death. As a result, the method of the present invention may include the biopsy of a portion of the treated target tissue to verify treatment efficacy immediately upon completion of each tissue treatment during the ongoing therapy procedure, while the patient is still in position for additional, continued or further treatment.

Figure 13:
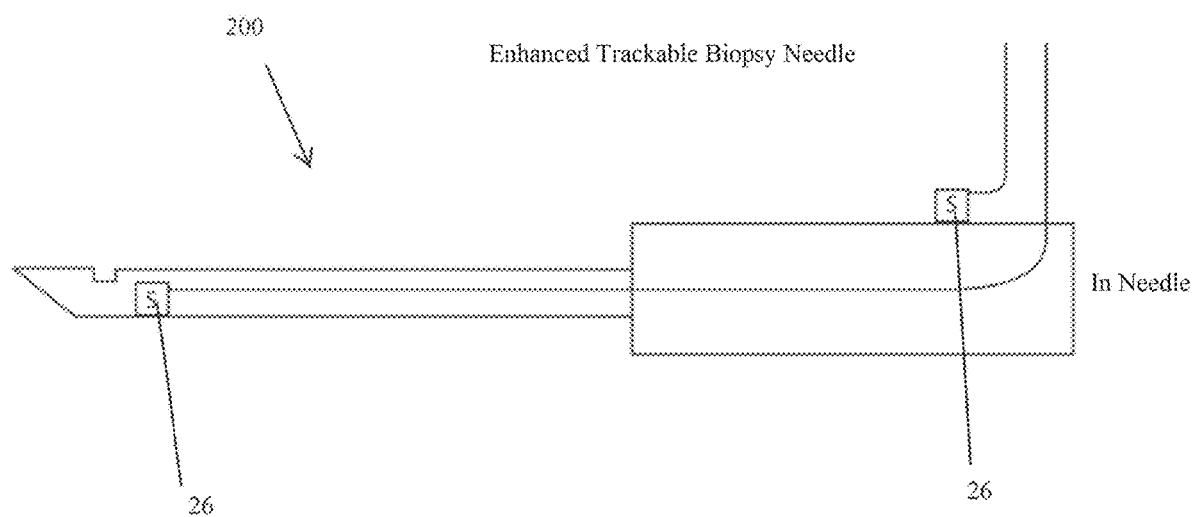
FIG. 13 is a schematic diagram of the enhanced trackable biopsy needle 200 according to the present invention.

A biopsy needle 200 suitable for this purpose is shown in FIG. 13. Like EMB treatment probes 20, biopsy needle 200 may comprise sensor/transmitters 26 (electromagnetic or otherwise) built into the needle and/or needle body to track the location of the biopsy tip of needle 200 and/or the orientation of the needle 200 as a whole. In certain embodiments, biopsy needle 200 may also comprise sensors to investigate tissue characteristics to determine cancerous from non-cancerous tissue and/or determine cellular content spillage in order to ascertain and/or document cancer cell death, such as those sensors described by Laufer and Miller, above.

Biopsy needle 200 is preferably operatively connected to SHCU 14 to provide real-time data from any sensors contained thereon and to enable real-time tracking of biopsy needle 200 by SHCU 14 to monitor treatment, as described in more detail below. Additional treatment may be immediately administered via, i.e., EMB treatment probe 20, based on the biopsy tissue inspection or result, and/or other information obtained torn the sensors on biopsy needle 200 or visual determination of treatment efficacy without removing biopsy needle 200 from the treatment area.

Trackable Anesthesia Needles 300

EMB, by virtue of its bipolar wave forms in the described frequency range, does not cause muscle twitching and contraction. Therefore a procedure using the same may be carried out under local anesthesia without the need for general anesthesia and neuromuscular blockade to attempt to induce paralysis during the procedure. Rather, anesthesia can be applied locally for the control of pain without the need for the deeper and riskier levels of sedation.

Figure 14:
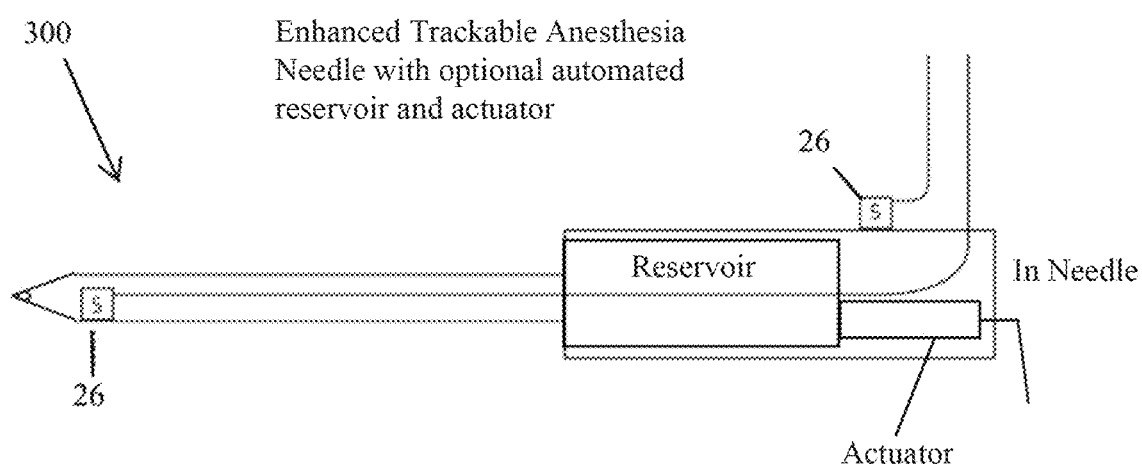
FIG. 14 is a schematic diagram of the enhanced trackable anesthesia needle 300 according to the present invention.
Figure 15:
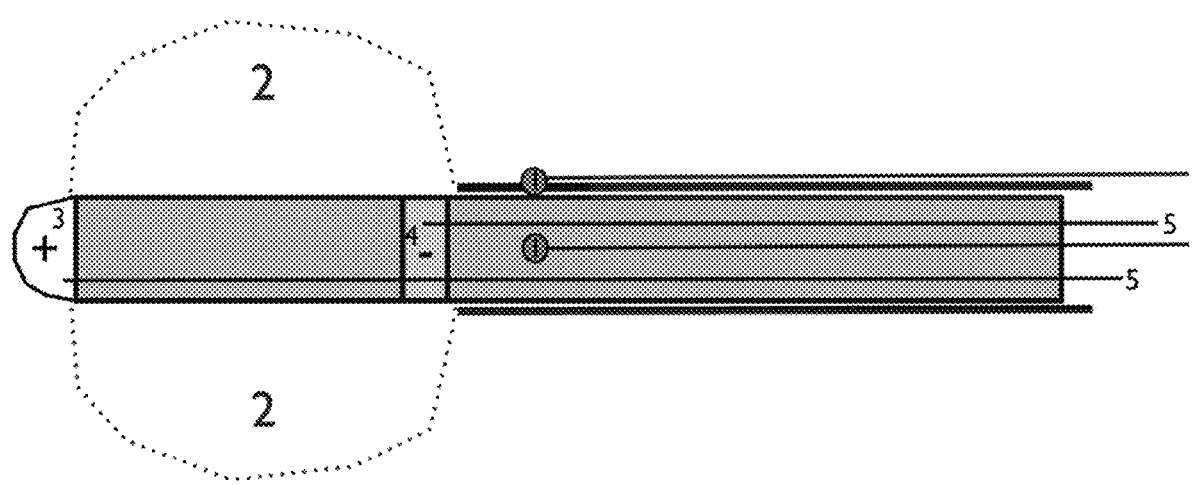
FIG. 15 is a schematic diagram depicting the positioning of a therapeutic EMB treatment probe 20 according to an embodiment of the present invention proximate the treatment area 2.
Figure 16:
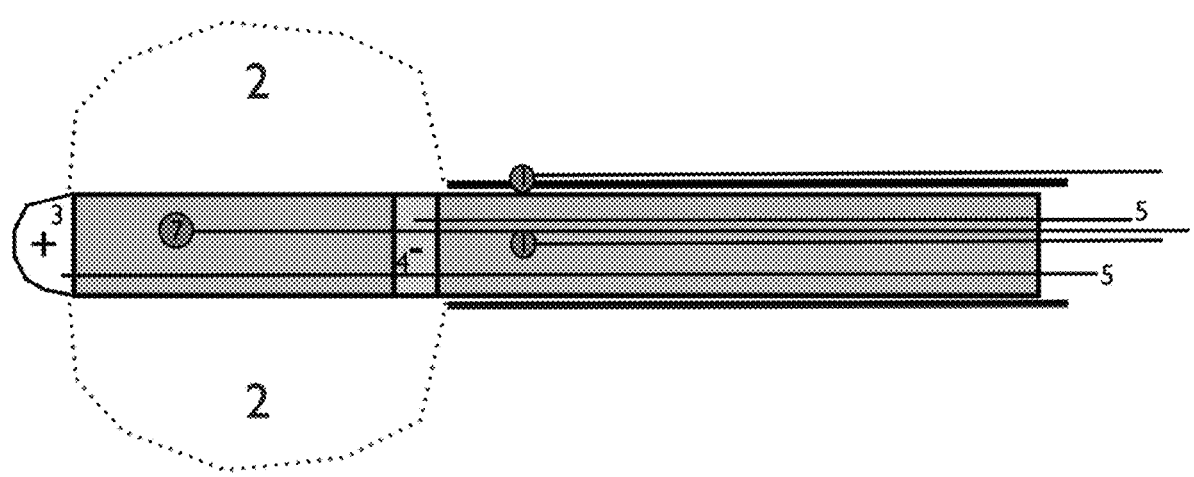
FIG. 16 is a schematic diagram depicting the positioning of a therapeutic EMB treatment probe 20 comprising a thermocouple 7 according to another embodiment of the present invention proximate the treatment area 2.

For this purpose, one or more trackable anesthesia needles 300 may be provided. With reference to FIG. 14, Anesthesia needles 300 may be of the type known in the art and capable of delivering anesthesia to the Neurovascular bundles or other potential treatment regions, including the point of entry of needle 300, EMB probe 20, biopsy probe 200 or any of the other devices described herein through the skin to enhance pain relief. Anesthesia needles 300 may also comprise sensor/transmitters 26 (electromagnetic or otherwise) built into the needle and/or needle body to track the location anesthesia needle 300, Anesthesia needles 300 are preferably operatively connected to SHCU 14 to enable real-time tracking of anesthesia needle 300 by SHCU 14 and/or to monitor administration of anesthesia, as described in more detail below.

Alternatively, trackable anesthesia needles 300 may be omitted in favor of conventional anesthesia needles which may be applied by the physician using conventional manual targeting techniques and using the insertion point, insertion path and trajectories generated by the software according to the present invention, as described in further detail below.

Software Hardware Control Unit (SHCU) 14 and Treatment System Software

Figure 3:
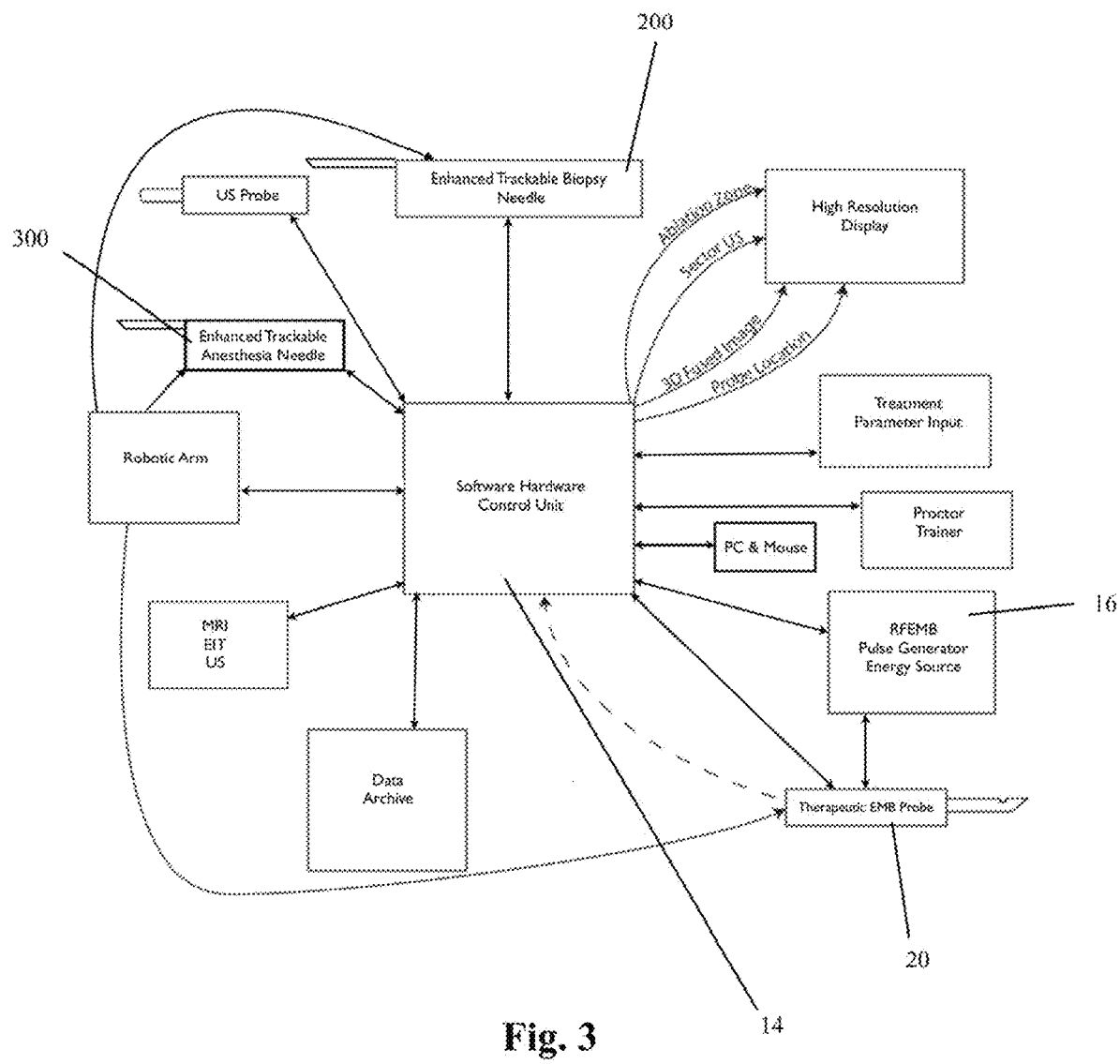
FIG. 3 is a schematic diagram of the software and hardware system according to the present invention.

With reference to FIG. 3, the Software Hardware Control Unit (SHCU) 14 is operatively connected to one or more (and preferably all) of the therapeutic and/or diagnostic probes/needles, imaging devices and energy sources described herein: namely, in a preferred embodiment, the SHCU 14 is operatively connected to one or more EMB pulse generator(s) 16, EMB treatment probe(s) 20, trackable biopsy needle(s) 200 and trackable anesthesia needle(s) 300 via electrical/manual connections for providing power to the connected devices as necessary and via data connections, wired or wireless, for receiving data transmitted by the various sensors attached to each connected device. SHCU 14 is preferably operatively connected to each of the devices described herein such as to enable SHCU 14 to receive all available data regarding the operation and placement of each of these devices. For example, SHCU 14 may be connected to one or more trackable anesthesia needles 300 via a fluid pump through which liquid medication is provided to anesthesia needle 300 such that SHCU 14 may monitor and/or control the volume, rate, type, etc. of medication provided through needle(s) 300.

In an alternative embodiment, SHCU 14 is also connected to one or more of the devices herein via at least one robot arm such that SHCU 14 may itself direct the placement of various aspects of the device relative to a patient, potentially enabling fully automatized and robotic treatment of certain cancerous tissues via EMB. It is envisioned that the system disclosed herein may be customizable with respect to the level of automation, i.e. the number and scope of components of the herein disclosed method that are performed automatically at the direction of the SHCU 14. At the opposite end of the spectrum from a fully automated system, SHCU 14 may operate software to guide a physician or other operator through a video monitor, audio cues, or some other means, through the steps of the procedure based on the software's determination of the best treatment protocol, such as by directing an operator where to place the EMB treatment probe 20, etc. As examples of semi-automation, SHCU 14 may be operatively connected to at least one robotic arm comprising an alignment tool capable of supporting probe 20, or providing an axis for alignment of probe 20, such that the tip of probe 20 is positioned at the correct point and angle at the surface of the patient's skin to provide a direct path, along the longitudinal axis of probe 20 to the preferred location of the tip of probe 20 within the treatment area. In another embodiment, as described in more detail below, SHCU 14 provides audio or visual cues to the operator to indicate whether the insertion path of probe 20 is correct. In each of these variations and embodiments, the system, at the direction of SHCU 14, directs the planning, validation and verification of the Predicted Ablation Zone (to be described in more detail below), to control the application of therapeutic energy to the selected region so as to assure proper treatment, to prevent damage to sensitive structures, to enhance the patient's immunologic response to his cancer and/or to provide tracking, storage, transmission and/or retrieval of data describing the treatment applied.

In a preferred embodiment, SHCU is a data processing system comprising at least one application server and at least one workstation comprising a monitor capable of displaying to the operator a still or video image, and at least one input device through which the operator may provide inputs to the system, i.e. via a keyboard/mouse or touch screen, which runs software programmed to control the system in three "modes" of operation, wherein each mode comprises instructions to direct the system to perform one or more novel features of the present invention. The software according to the present invention may preferably be operated from a personal computer connected to SHCU 14 via a direct, hardwire connection or via a communications network, such that remote operation of the system is possible. The three contemplated modes are Biopsy mode, Planning Mode and Treatment Mode. However, it will be understood to one of ordinary skill in the art that the software and/or operating system may be designed differently while still achieving the same purposes. In all modes, the software can create, manipulate, and display to the user via a video monitor accurate, real-time three-dimensional images of the human body, which images can be zoomed, enlarged, rotated, animated, marked, segmented and referenced by the operator via the system's data input device(s). As described, above, in various embodiments of the present invention the software and SHCU 14 can partially or fully control various attached components, probes, needles or devices to automate various functions of such components, probes, needles or devices, or facilitate robotic or remote control thereof.

Biopsy Mode

The SHCU is preferably operatively connected to one or more external imaging sources such as an magnetic resonance imaging (MRI), ultrasound (US), electrical impedance tomography (EIT), or any other imaging device known in the art and capable of creating images of the human body. Using inputs from these external sources, the SHCU first creates one or more "3D Fused Images" of the patient's body in the region of the detected cancer. The 3D Fused Images provide a 3D map of the selected treatment area within the patient's body over which locational data obtained from the one or more probes or needles according to the present invention may be overlaid to allow the operator to monitor the treatment in real-time against a visual of the actual treatment area. Preferably, after the creation of a 3D Fused Image, a biopsy of the imaged area is taken (either immediately or at the convenience of the physician/patient).

In a first embodiment, a 3D Fused Image would be created from one or more MRI and ultrasound image(s) of the same area of the patient's body. An MRI image used for this purpose may comprise a multi-parametric magnetic resonance image created using, i.e., a 3.0 Telsa MRI scanner (such as Achieva, manufactured by Philips Healthcare) with a 16-channel cardiac surface coil (such as a SENSE coil, manufactured by Philips Healthcare) placed over the pelvis of the patient with an endorectal coil (such as the BPX-30, manufactured by Medrad). MRI sequences obtained by this method preferably include: a tri-planar T2-weighted image, axial diffusion weighted imaging with apparent diffusion coefficient (ADC) mapping, 3-dimensional point resolved spatially localized spectroscopy, and an axial dynamic contrast enhanced MRI. An ultrasound image used for this purpose may be one or more 2D images obtained from a standard biplane transrectal ultrasound probe (such as the Hitachi EUB 350). The ultrasound image may be formed by, i.e., placing an EM field generator (such as that manufactured by Northern Digital Inc.) above the pelvis of the patient, which allows for real-time tracking of a custom ultrasound probe embedded with a passive EM tracking sensor (such as that manufactured by Traxtal, Inc.).

The 3D fused image is then formed by the software according to the present invention by encoding the ultrasound data using a position encoded prostate ultrasound stepping device (such as that manufactured by Civco Inc) and then overlaying a virtual brachytherapy grid over the 3D ultrasound fused MRI image. A brachytherapy grid is positionally correlated to the resultant image by its fixed position to the US probe by the US stepping device. Thus, in this embodiment, biopsy needle 200 does not need a locational sensor 26 because the positional guidance is provided by the brachytherapy grid. The software according to the present invention also records of the position of the obtained biopsy tor Utter use in guiding therapy.

This protocol thus generates a baseline, diagnostic 3D Fused Image and displays the diagnostic 3D Fused Image to the operator in real time via the SHCU video monitor. Preferably, the system may request and/or receive additional 3D ultrasound images of the treatment area during treatment and fuse those subsequent images with the baseline 3D Fused image for display to the operator.

As an alternate means of creating the 3D Fused. Image, a 2-dimensional TRUS sweep of the prostate is performed in the axial plane to render a three-dimensional ultrasound image that is then registered and fused to a pre-biopsy MRI using landmarks common to both the ultrasound image and MRI image such as the capsular margins of the prostate and urethra. Lesions suspicious for cancer identified on MRI are semi-automatically superimposed on the real-time TRUS image. A biopsy device (such as that manufactured by Bard, Inc.) and embedded with a passive EM tracking device, as previously described, can then be tracked in relation to the position of the prostate and thus a biopsy performed.

In yet another embodiment, the 3D Fused Image may be created by placing the patient in the dorsal lithotomy position, placing a biopsy grid on the perineum, inserting a TRUS probe into the rectum and placing the transducer in the proper position prior to 3D data acquisition at the lateral margin of the prostate. The operator then activates the ultrasound probe to capture multiple images. The computer then reconstructs a 3D image of the prostate by displaying the image in a multi-planer reformation (MPR) mode and displays grid lines through the 3D volume that correspond to the holes in the grid on the patient's perineum. At this point, the reconstructed MRI data can be fused to the ultrasound date using the previously described methods. Such a system was described in Onik G M, Downey D B, Fenster A, *Sonographically Monitoring Cryosurgery In A Prostate Phantom*, Journal of Ultrasound 16:267-270 (1996), which disclosure is incorporated herein in its entirety.

The 3D Fused image as created by any one of the above methods is then stored in the non-transitive memory of the SHCU, which may employ additional software to locate and electronically tag within the 3D Fused Image specific areas in the prostate or its vicinity, including sensitive or critical structures and areas that require anesthesia such as the Neurovascular Bundles, i.e. to enable the guidance of standard or trackable anesthesia needles to those locations. The SHCU then displays the 3D Fused Image to the operator alone or overlaid with locational data from each of the additional devices described herein where available. The 3D Fused Image may be presented in real time in sector view, or the software may be programmed to provide other views based on design preference. As described above, the software may then direct the operator and/or a robotic arm to take a biopsy of the identified area of cancerous tissue or in a specific location of concern based on an analysis of the imaging data and record the results of same, which biopsy may be tracked in real time. Analysis of the biopsy tissue, which may be done by the system or a physician/technician, will indicate whether the biopsied tissue is cancerous. Thus, a 3D map of cancerous tissue in the area of concern within the patient's body may be created in this way. The software may employ an algorithm to determine where individual biopsies should be taken based on optimal spacing between same or based on the location of other biopsies that revealed cancerous tissue to ensure that all areas of cancerous tissue in the region have been located and indexed against the 3D Fused Image.

Using the biopsy result data in conjunction with the 3D Fused Image, the software can create a "3D Mapped Biopsy Fused Image", which can be used as the basis for an office based treatment procedure for the patient (see FIGS.

7A-7B). The SHCU also preferably stores the biopsy sample information indexed to sample location, orientation and number, which information can be provided to a pathologist or other treatment provider via a communications network to be displayed on his or her remote workstation, allowing the other treatment provider to interact with and record pathological findings about each sample in real time.

Planning Mode

Upon generation of one or more 3D Fused Images of the planned treatment area and, preferably completion of one or more biopsies of the affected area, the SHCU may display to the operator via a video terminal the precise location(s) of one or more areas in the prostate (or other treatment area), or its vicinity, which require therapy, via annotations or markers on the 3D Fused image(s); this area requiring therapy is termed the Target Treatment Zone. This information is then used by the system or by a physician to determine optimal placement of the EMB treatment probe(s) 20. Importantly, the 3D Fused Image should also contain indicia to mark Neurovascular Bundles (NVB), the location of which will be used to calculate a path for placement of one or more anesthesia needles for delivery of local anesthesia to the treatment area. If necessary due to changes in gland size, the geographic location of each marker can be revised and repositioned, and the 3D Fused Image updated in real time by the software, using 3D ultrasound data as described above. The system may employ an algorithm for detecting changes in gland size and requesting additional ultrasound scans, may request ultrasound scans on a regular basis, or the like.

In a preferred embodiment, the software may provide one or more "virtual" EMB treatment probes 20 which may be overlaid onto the 3D Fused Image by the software or by the treatment provider to determine the extent of ablation that would be accomplished with each configuration. The virtual probes also define a path to the target point by extending a line or path from the target point to a second point defining the entry point on the skin surface of the patient for insertion of the real EMB treatment probe. Preferably, the software is configured to test several possible probe 20 placements and calculate the probable results of treatment to the affected area via such a probe 20 (the Predicted Ablation Zone) placement using a database of known outcomes from various EMB treatment protocols or by utilizing an algorithm which receives as inputs various treatment parameters such as pulse number, amplitude, pulse width, and frequency. By comparing the outcomes of these possible probe locations to the tumor volume as indicated by the 3D Fused linage, the system may determine the optimal probe 20 placement. Alternatively, the system may be configured to receive inputs from a physician to allow him or her to manually arrange and adjust the virtual EMB treatment probes to adequately cover the treatment area and volume based on his or her expertise. The system may utilize virtual anesthesia needles in the same way to plan treatment.

When the physician is satisfied with the Predicted Ablation Zone coverage shown on the Target Treatment Zone based on the placement and configuration of the virtual EMB treatment probes and the virtual anesthesia needles, as determined by the system of by the physician himself, the physician "confirms" in the system (i.e., "locks in") the three-dimensional placement and energy/medication delivery configuration of the grouping of virtual EMB treatment probes and virtual anesthesia needles, and the system registers the position of each as an actual software target to be overlaid on the 3D Fused Image and used by the system for guiding the insertion of the real probe(s) and needle(s) according to the present invention (which may be done automatically by the system via robotic arms or by the physician by tracking his or her progress on the 3D Fused Image.

If necessary, EMB treatment, as described in further detail below, may be carried out immediately after a biopsy of the patient is performed. Alternately, EMB treatment may take place days or even weeks after one or more biopsies are performed. In the latter case, the steps described with respect to the Planning Mode, above, may be undertaken by the software/physician at any point between biopsy(s) and treatment.

Treatment Mode

The software displays, via the SHCU video monitor, the previously confirmed and "locked in" Target Treatment Zone, Predicted Ablation Zone and 3D Mapped Biopsy Fused Image, with the location and configuration of all previously confirmed virtual probes/needles and their calculated insertion points, angular 3D geometry, and insertion depths, which can be updated as needed at time of treatment to reflect any required changes as described above.

Using the planned locations and targets established for the delivery of anesthesia, and the displayed insertions paths, the software then guides the physician (or robotic arm) in real time to place one or more anesthesia needles and then to deliver the appropriate amount of anesthesia to the targeted locations (i.e., in the vicinity of the Neurovascular Bundles). Deviations from the insertion path previously determined by the system in relation to the virtual needles/probes may be highlighted by the software in real time so as to allow correction of targeting at the earliest possible time in the process. This same process allows the planning and placement of local anesthesia needles as previously described. In some embodiments, the system may employ an algorithm to calculate the required amount of anesthesia based on inputs such as the mass of the tissue to be treated and individual characteristics of the patient which may be inputted to the system manually by the operator or obtained from a central patient database via a communications network, etc.

Once anesthesia has been administered, the system displays the Predicted Ablation Zone and the boundaries thereof as an overlay on the 3D Fused Image including the Target Treatment Zone and 3D Mapped Biopsy Fused Image and directs the physician (or robotic arm) as to the placement of each EMB treatment probe 20. The Predicted Ablation Zone may be updated and displayed in real time as the physician positions each probe 20 to give graphic verification of the boundaries of the Target Treatment Zone, allowing the physician to adjust and readjust the positioning of the Therapeutic EMB Probes, sheaths, electrode exposure and other treatment parameters (which in turn are used to update the Predicted Ablation Zone). When the physician (or, in the case of a fully automated system, the software) is confident of accurate placement of the probes, he or she may provide such an input to the system, which then directs the administration of EMB pulses via the EMB pulse generator 16 and probes 20.

The SHCU controls the pulse amplitude 30, frequency 31, polarity and shape provided by the EMB pulse generator 16, as well as the number of pulses 32 to be applied in the treatment series or pulse train, the duration of each pulse 32, and the inter pulse burst delay 33. Although only two are depicted in FIG. 10 due to space constraints, EMB ablation is preferably performed by application of a series of not less than 100 electric pulses 32 in a pulse train so as to impart the energy necessary on the target tissue 2 without developing thermal issues in any clinically significant way. The width of each individual, pulse 32 is preferably from 100 to 1000 μs with an inter pulse burst interval 33 during which no voltage is applied in order to facilitate heat dissipation and avoid thermal effects. The relationship between the duration of each pulse 32 and the frequency 31 (period) determines the number of instantaneous charge reversals experienced by the cell membrane during each pulse 32. The duration of each inter pulse burst interval 33 is determined by the controller 14 based on thermal considerations. In an alternate embodiment the system is further provided with a temperature probe 22 inserted proximal to the target tissue 2 to provide a localized temperature reading at the treatment site to the SHCU 14. The temperature probe 22 may be a separate, needle type probe having a thermocouple tip, or may be integrally formed with or deployed from one or more of the needle electrodes, or the Therapeutic EMB Probes. The system may further employ an algorithm to determine proper placement of this probe for accurate readings from same. With temperature feedback in real time, the system can modulate treatment parameters to eliminate thermal effects as desired by comparing the observed temperature with various temperature set points stored in memory. More specifically, the system can shorten or increase the duration of each pulse 32 to maintain a set temperature at the treatment site to, for example, create a heating (high temp) for the needle tract to prevent bleeding or to limit heating (low temp) to prevent any coagulative necrosis. The duration of the inter pulse burst interval can be modulated in the same manner in order to eliminate the need to stop treatment and maximizing the deposition of energy to accomplish EMB. Pulse amplitude 30 and total number of pulses in the pulse train may also be modulated for the same purpose and result.

Figure 6:
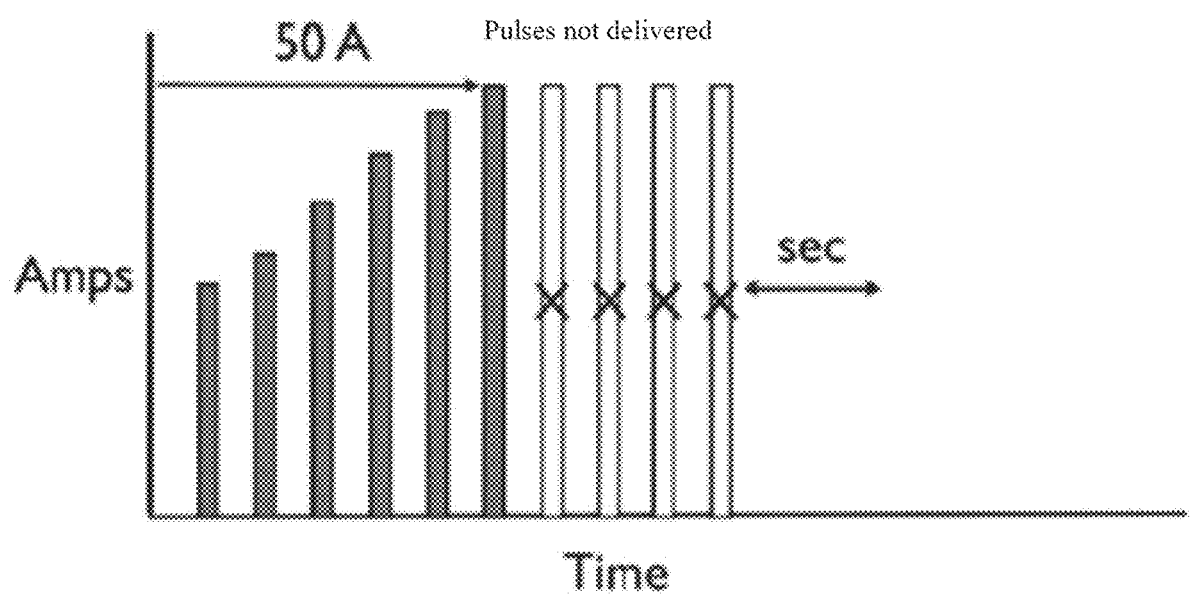
FIG. 6 is a diagram of a prior art failure to deliver prescribed pulses due to excess current.
Figure 7A:
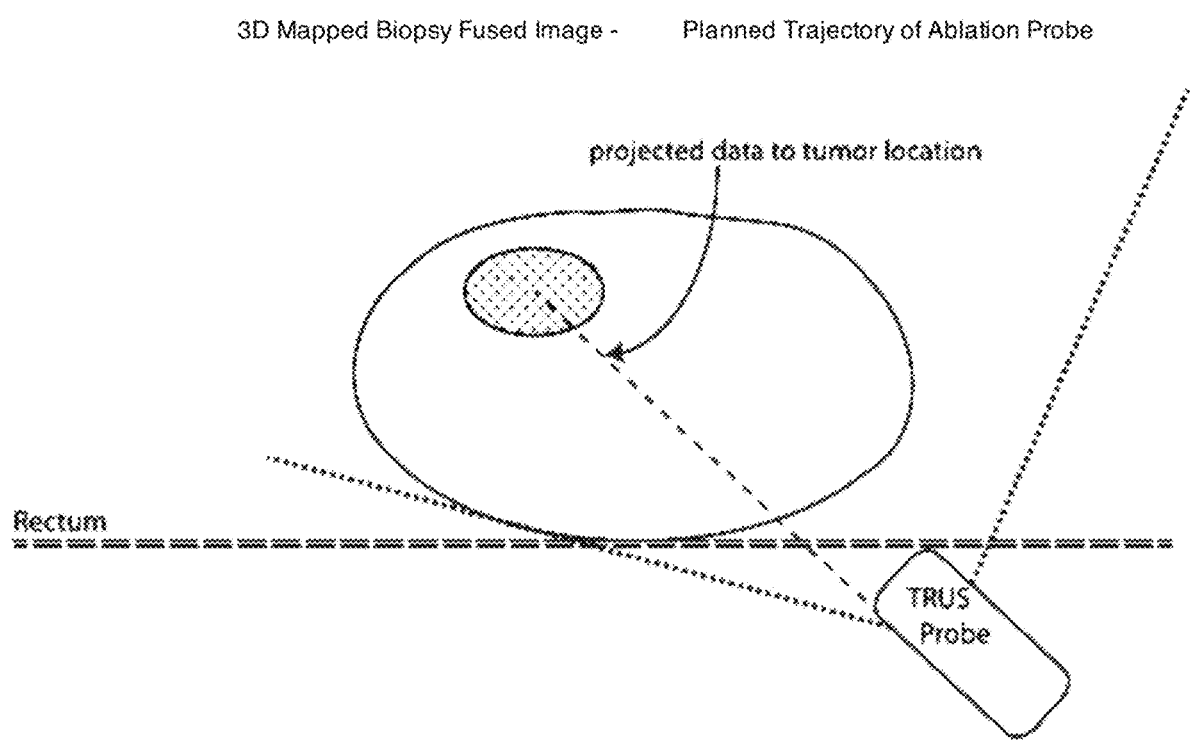
FIG. 7A is a schematic diagram depicting a TRUSS scan of a suspect tissue mass.
Figure 7B:
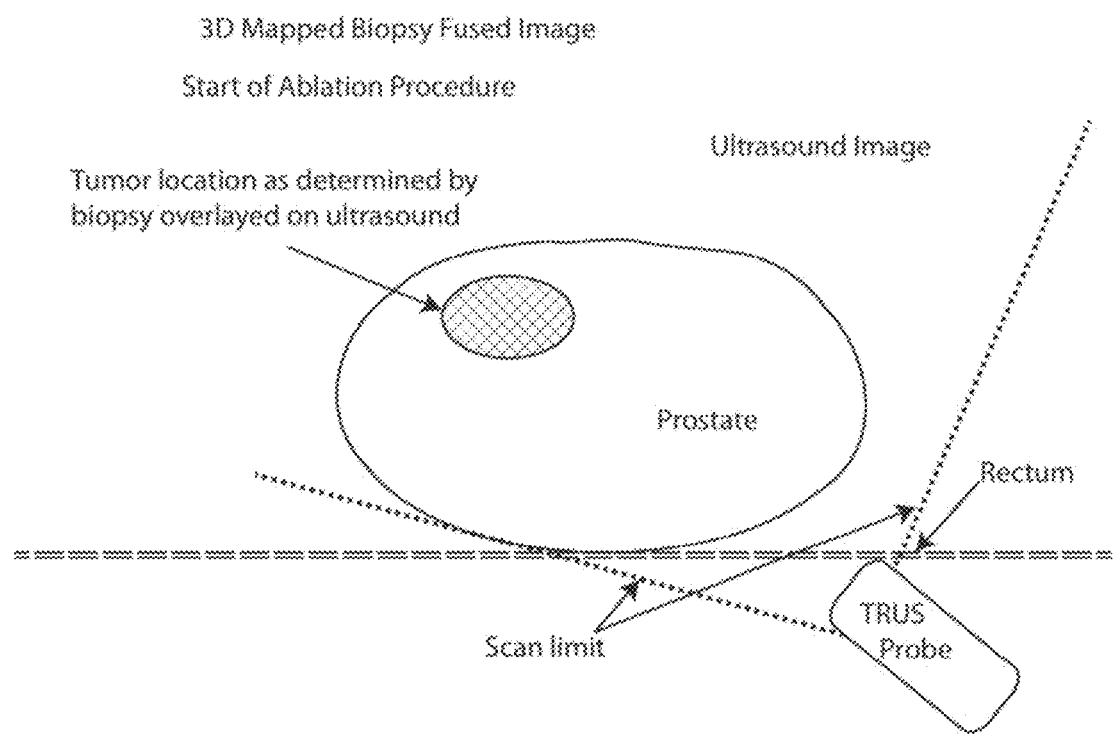
FIG. 7B is a schematic diagram depicting the results of a 3D Fused Image of a suspect tissue mass.
Figure 8:
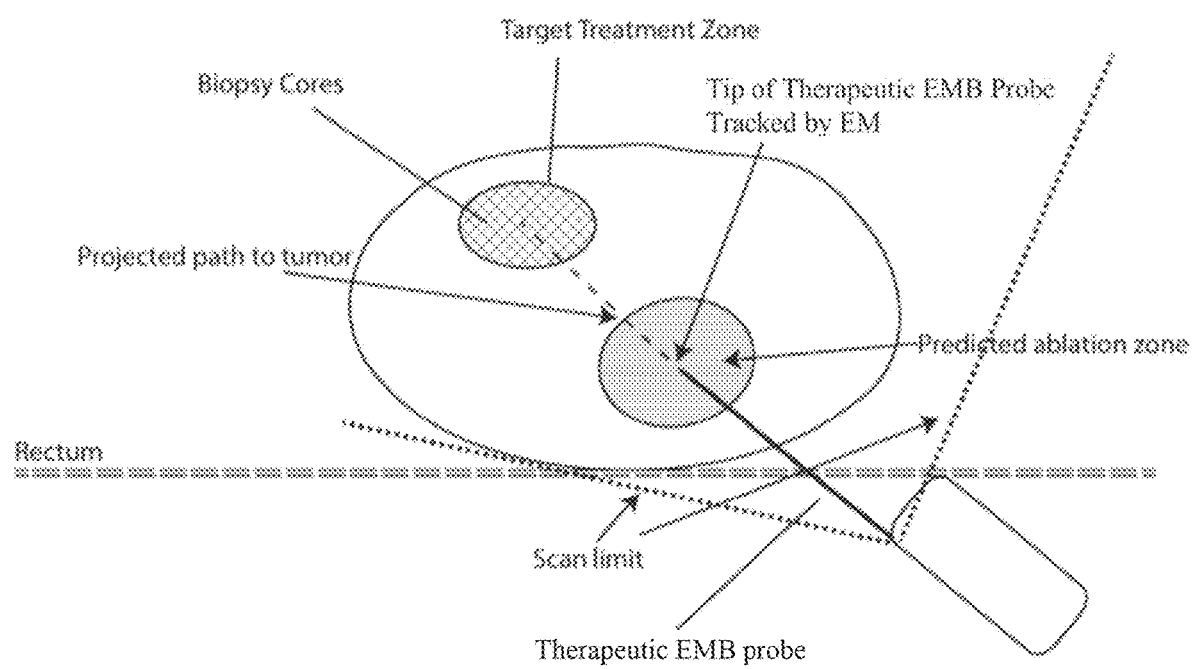
FIG. 8 is a schematic diagram depicting the target treatment area and Predicted Ablation Zone relative to a therapeutic EMB treatment probe 20 prior to delivering treatment.

In yet another embodiment, the SHCU may monitor or determine current flow through the tissue during treatment for the purpose of avoiding overheating while yet permitting treatment to continue by reducing the applied voltage. Reduction in tissue impedance during treatment due to charge buildup and membrane rupture can cause increased current flow which engenders additional heating at the treatment site. With reference to FIG. 6, prior treatment methods have suffered from a need to cease treatment when the current exceeds a maximum allowable such that treatment goals are not met. As with direct temperature monitoring, the present invention can avoid the need to stop treatment by reducing the applied voltage and thus current through the tissue to control and prevent undesirable clinically significant thermal effects. Modulation of pulse duration and pulse burst interval duration may also be employed by the controller 14 for this purpose as described.

During treatment, the software captures all of the treatment parameters, all of the tracking data and representational data in the Predicted Ablation Zone, the Target Treatment Zone and in the 3D Mapped Biopsy Fused Image as updated in real time to the moment of therapeutic trigger. Based on the data received by the system during treatment, the treatment protocol may be adjusted or repeated as necessary.

The software may also store, transmit and/or forwarding treatment data to a central database located on premises in the physician's office and/or externally via a communications network so as to facilitate the permanent archiving and retrieval of all procedure related data. This will facilitate the use and review of treatment data, including for diagnostic purposes and pathology related issues, for treatment review purposes and other proper legal purposes including regulatory review.

The software may also transmit treatment data in real time to a remote proctor/trainer who can interact in real time with the treating physician and all of the images displayed on the screen, so as to insure a safe learning experience for an inexperienced treating physician, and so as to archive data useful to the training process and so as to provide system generated guidance for the treating physician. In another embodiment, the remote proctor can control robotically all functions of the system.

Optionally, with one or more EMB treatment probes 20 still in place within the ablated tissue, the physician or system can perform injection of immunologic adjuvant agents, or other materials into the ablated tissue, using capabilities built into the probe, as described above, or through separate delivery means.

In other embodiments of the present invention, some or all of the treatment protocol may be completed by robotic arms, which may include an ablation probe guide which places the specially designed Therapeutic EMB Probe (or an ordinary ablation probe but with limitations imposed by its design) in the correct trajectory to the tumor. Robotic arms may also be used to hold the US transducer in place and rotate it to capture images for a 3D US reconstruction. Robotic arms can be attached to an anesthesia needle guide which places the anesthesia needle in the correct trajectory to the Neurovascular Bundles to guide the delivery of anesthesia by the physician.

In other embodiments, the robotic arm can hold the anesthesia needle itself or an trackable anesthesia needle (see FIG. 14) with sensor-transmitters and actuators built in, that can be tracked in real time, and that can feed data to the software to assure accurate placement thereof and enable the safe, accurate and effective delivery of anesthesia to the Neurovascular bundles and other regions, and can directly insert the needle into the targeted areas of the Neurovascular Bundle and other regions using and reacting robotically to real time positioning data supported by the 3D Mapped Biopsy Fused Image and Predicted Ablation Zone data and thereby achieving full placement robotically, and upon activation of the flow actuators, the delivery of anesthesia as planned or confirmed by the physician.

In addition, the robotic arm can hold the Therapeutic EMB Probe itself and can directly insert the probe into the patients tumor using and reacting robotically to real time positioning data supported by the 3D Mapped Biopsy Fused Image and Predicted Ablation Zone data and thereby achieving full placement robotically.

Robotic components capable of being used for these purposes include the iSR'obot™ Mona Lisa robot, manufactured by Biobot Surgical Pte. Ltd. In such embodiments the Software supports industry standard robotic control and programming languages such as RAIL, AML, VAL, AL, RPL, PYRO, Robotic Toolbox for MATLAB and OPRoS as well as other robot manufacturer's proprietary languages.

In yet another embodiment, tissue characterization ability which is built into the EMB probe itself can identify the cancerous area and then allow direct destruction of the tumor in a one step procedure eliminating the need for the separate biopsy and pathological examination.

The SHCU can fully support Interactive Automated Robotic Control through a proprietary process for image sub-segmentation of prostate structures for planning and performing robotically guided transperineal biopsy and therapeutic interventions in an office based setting.

Sub-segmentation is the process of capturing and storing precise image detail of the location size and placement geometry of the described object so as to be able to define, track, manipulate and display the object and particularly its three-dimensional boundaries and accurate location in the body relative to the rest of the objects in the field and to the anatomical registration of the patient in the system so as to enable accurate three-dimensional targeting of the object or any part thereof, as well as the three-dimensional location of its boundaries in relation to the locations of all other subsegmented objects and computed software targets and needle and probe pathways. The software sub-segments out various critical prostate substructures, such as the neurovascular bundles, peripheral zone, ejaculatory ducts, urethra, rectum, and Denonvilliers Fascia in a systematic and programmatically supported and required fashion, which is purposefully designed to provide and enable the component capabilities of the software as described herein.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

We claim:

1. A system for ablating undesirable soft tissue in a living subject using radio frequency electrical membrane breakdown (RF-EMB), comprising:
    an electric pulse generator configured to produce a bi-polar pulse, wherein the bi-polar pulse is characterized by an instant charge reversal between a positive and a negative polarity;
    at least one therapeutic probe comprising at least one electrode operatively connected to said electric pulse generator, said therapeutic probe and electric pulse generator configured to apply to said soft tissue an electric field in a range of 1,500 V/cm to 10,000 V/cm, wherein the applied electric field in the range of 1,500 V/cm to 10,000 V/cm and the bi-polar pulse produced by the electric pulse generator are sufficient to cause RF-EMB, wherein RF-EMB is characterized by immediate destruction of a cell membrane of a plurality of cells of said soft tissue, immediate spillage of non-denatured intracellular components into an extracellular space, and exposure of an internal constituent part of said cells and said cell membrane to said extracellular space;
    one or more retractable needles configured to administer one or more immunologic response enhancing drugs intratumorally to the undesirable soft tissue;
    a biopsy needle; and
    a controller operatively connected to said electric pulse generator, said therapeutic probe and said biopsy needle.

2. The system of claim 1, wherein the at least one therapeutic probe further comprises:
    a core formed of an electrically conductive material;
    an outer electrode covering said core on at least one side; and
    a first insulating sheath formed of a non-electrically-conductive material, said first insulating sheath forming a barrier between said core and said outer electrode.

3. The system of claim 2, wherein said outer electrode is mounted on said first insulating sheath, and wherein said outer electrode and said first insulating sheath are movable as a unit along a lateral dimension of said core to enable adjustment of the lateral distance between a distal end of said core and said outer electrode.

4. The system of claim 2, further comprising at least one electromagnetic sensor on each of said core and said outer electrode.

5. The system of claim 2, wherein said at least one therapeutic probe comprises at least one sensor configured to determine cell death in tissue in the vicinity of said at least one sensor.

6. The system of claim 2, wherein the at least one therapeutic probe comprises a hollow interior defined by an inner lumen configured to accommodate a surgical tool.

7. The system of claim 6, wherein said outer electrode is on an outer surface of the therapeutic probe, and further comprising a needle sized to fit within said inner lumen of said therapeutic probe, said needle comprising a needle electrode on a distal end thereof, wherein a polarity of said needle electrode is different than a polarity of said outer electrode.

8. The system of claim 2, wherein said at least one therapeutic probe comprises an expandable balloon at a distal end thereof, said expandable balloon comprising one or more electrodes for delivering said electric field.

9. The system of claim 2, wherein said at least one therapeutic probe is a catheter-type probe, wherein said at least one therapeutic probe further comprises:
    a lumen;
    a positive electrode disposed at a first location on an outer surface of said therapeutic probe; and
    a negative electrode disposed at a second location on the outer surface of said therapeutic probe, said first location and said second location being separated along a longitudinal dimension of said at least one therapeutic probe.

10. The system of claim 9, wherein one of said positive electrode or said negative electrode is disposed on the end of a second insulating sheath formed of the non-electrically-conductive material, said second insulating sheath being movable along a longitudinal axis of said at least one therapeutic probe.

11. The system of claim 1, wherein the biopsy needle is trackable.

12. The system of claim 1, wherein said at least one therapeutic probe is semi-flexible or flexible.

13. The system of claim 1, wherein at least a portion of said system is configured to be robotically controlled.

14. The system of claim 13, wherein the therapeutic probe is configured to be robotically positioned using a robotic arm.

15. The system of claim 1, further comprising a temperature probe.

16. The system of claim 15, wherein the temperature probe comprises a thermocouple, and wherein the temperature probe is integral with the therapeutic probe.

17. The system of claim 15, wherein the bi-polar pulse is configured to be altered based on an output from the temperature probe.

18. The method of claim 1, wherein the one or more retractable needles are configured to deliver a composition comprising a combination of at least two immune checkpoint inhibitors and an immunomodulatory agent, each being present in a therapeutically effective amount, wherein the at least two immune checkpoint inhibitors are a CTLA-4 inhibitor and a PD-1 inhibitor.

19. The method of claim 18, wherein the immunomodulatory agent comprises an agent capable of modulating myeloid cell functions.

20. The method of claim 19, wherein the immunomodulatory agent comprises Tasquinimod.

21. The method of claim 18, wherein the at least two immune checkpoint inhibitors comprise a PD-L1 inhibitor.

* * * * *